(12) United States Patent
Jesneck et al.

(10) Patent No.: US 11,145,407 B1
(45) Date of Patent: Oct. 12, 2021

(54) DATA MANAGEMENT SYSTEM FOR TRACKING AND OPTIMIZING MEDICAL CLINICAL PERFORMANCE

(71) Applicant: Firefly Lab, LLC, Wilmington, DE (US)

(72) Inventors: Jonathan Lee Jesneck, Lake Oswego, OR (US); Ruchi Mrugesh Thanawala, Lake Oswego, OR (US)

(73) Assignee: Firefly Lab, LLC, Wilmington, DE (US)

( * ) Notice: Subject to any disclaimer, the term of this patent is extended or adjusted under 35 U.S.C. 154(b) by 0 days.

(21) Appl. No.: 16/853,160

(22) Filed: Apr. 20, 2020

Related U.S. Application Data

(60) Provisional application No. 62/836,792, filed on Apr. 22, 2019.

(51) Int. Cl.
*G16H 40/20* (2018.01)
*G16H 50/20* (2018.01)

(52) U.S. Cl.
CPC ............. *G16H 40/20* (2018.01); *G16H 50/20* (2018.01)

(58) Field of Classification Search
CPC .............................. G16H 40/20; G16H 50/20
See application file for complete search history.

(56) References Cited

U.S. PATENT DOCUMENTS

| 5,788,504 | A | 8/1998 | Rice et al. |
|---|---|---|---|
| 6,119,097 | A | 9/2000 | Ibarra |
| 6,157,808 | A | 12/2000 | Hollingsworth |
| 7,181,413 | B2 | 2/2007 | Hadden et al. |
| 8,082,172 | B2 | 12/2011 | Chao et al. |
| 8,285,585 | B2 | 10/2012 | Chao et al. |
| 8,768,752 | B1 | 7/2014 | Buckelew |
| 10,510,268 | B2 | 12/2019 | Gmeiner et al. |
| 2010/0266998 | A1* | 10/2010 | Tashiro ................. G09B 23/28 434/262 |
| 2014/0172441 | A1* | 6/2014 | Melamed ........... G06Q 30/0202 705/2 |
| 2018/0018634 | A1* | 1/2018 | Satagopan ....... G06Q 10/06398 |

OTHER PUBLICATIONS

Abbott, K.L. et al., "Number of Operative Performance Ratings Needed to Reliably Assess the Difficulty of Surgical Procedures", 2019, Journal of Surgical Ed., 76:6, e189-192.

(Continued)

*Primary Examiner* — Michael Tomaszewski
*Assistant Examiner* — Mohmad Muqueeth
(74) *Attorney, Agent, or Firm* — Wiggin and Dana LLP; Anthony D. Sabatelli; Thomas M. Landman

(57) ABSTRACT

The present invention relates to a web-based platform to track medical clinical assignments and to link embedded evaluation instruments to procedure type, for the optimization and improvement of medical clinical education and performance for healthcare professions, and in particular for graduate residents, such as surgical residents. This model is the basis for the platform for physician scoring and profiling to determine physician educational and performance competency with a selected medical procedure. The invention provides methods and systems for improving or optimizing performance tracking of a medical professional.

8 Claims, 28 Drawing Sheets

(56) References Cited

OTHER PUBLICATIONS

Abid, M.A. et al., "Patient Outcomes as a Measure of Surgical Technical Skills", 2016, Otorinolaringologia, 66:4, pp. 99-106.

ACGME Program Requirements for Graduate Medical Education in General Surgery, Revised Jul. 1, 2019, pp. 1-61, PDF Retrieved from Internet: <www.acgme.org>.

Ahmed, N. et al., "A systematic review of the effects of resident duty hour restrictions in surgery", 2014, Annals of Surgery, 259:6, pp. 1041-1053.

AMA Current Procedural Terminology. Retrieved on Apr. 25, 2020. Retrieved from Internet: <www.ama-assn.org>.

Anderson, P.A. et al., "Giving feedback on clinical skills: are we starving our young?" 2012, Journal of Graduate Medical Education, 4, pp. 154-158.

Bell, R.H. Jr., "Why Johnny cannot operate", 2009, Surgery, 146:4, pp. 533-542.

Berg B.A., "Markov Chain Monte Carlo Simulations and Their Statistical Analysis" Singapore. World Scientific Publishing Co. Pte. Ltd., 2004, 54 pages.

Birkmeyer, J.D. et al. "Michigan Bariatric Surgery Collaborative. Surgical skill and complication rates after bariatric surgery", 2013, N. Engl. J. Med., 369:15, pp. 1434-1442.

Bohnen, J.D. et al., "The Feasibility of Real-Time Intraoperative Performance Assessment With SIMPL", 2016, J. Surg. Educ., 73:6, pp. e118-e130.

Bucholz, E.M. et al., "Our trainees' confidence results from a national survey of 4136 US general surgery residents", 2011, Arch. Surg. 146:8, pp. 907-914.

Coombs, W.T. et al., "Univariate and multivariate omnibus hypothesis tests selected to control Type I error rates" 1996, Review of Educational Research, 66:2, pp. 137-179.

Corder, G.W. et al., "Nonparametric Statistics: A Step-by-Step Approach" 2009, Hoboken, New Jersey, Wiley.

Cox, T. et al., "Moving the Needle: Simulation's Impact on Patient Outcomes", 2015, Surg. Clin. North Am., 95:4, pp. 827-838.

Darosa, D.A. et al., "A Theory-Based Model for Teaching and Assessing Residents in the Operating Room", 2013, Journal of Surgical Education, 70, pp. 24-30.

De Blacam, C. et al., "Are residents accurate in their assessments of their own surgical skills?", 2012, The American Journal of Surgery, 204:5, pp. 724-731.

Dougherty, P. et al., "Intraoperative assessment of residents", 2013, J Grad Med. Educ., 5, pp. 333-334.

Drake, F.T. et al., "The general surgery chief resident operative experience: 23 years of national ACGME case logs", 2013, JAMA Surg., 148:9, pp. 841-847.

Eaton, M. et al., "Value and barriers to use of a SIMPL tool for resident feedback", 2019, Journal of Surgical Education, 76, pp. 620-627.

Fryer, J.P. et al., "Effect of Ongoing Assessment of Resident Operative Autonomy on the Operating Room Environment", 2018, J. Surg. Educ., 75:2, pp. 333-343.

Gas, B.L. et al. "Objective Assessment of General Surgery Residents Followed by Remediation", 2016, J. Surg. Educ., 73:6, pp. e71-e76.

George, B.C. et al. "Reliability, validity, and feasibility of the Zwisch scale for the assessment of intraoperative performance", 2014, J. Surg. Educ., 71:6, pp. e90-e96.

Gofton, W.T. et al. "The Ottawa Surgical Competency Operating Room Evaluation (O-SCORE): a tool to assess clinical competence", 2012, Acad. Med., 87:10, pp. 1401-1407.

Gundle, K.R. et al. "Rapid Web-Based Platform for Assessment of Orthopedic Surgery Patient Care Milestones: A 2-Year Validation", 2017, J. Surg. Ed., 74:6, pp. 1116-1123.

Hanks, J.B. "Simulation in Surgical Education: Influences of and Opportunities for the Southern Surgical Association", 2019, J. Am. Coll. Surg., 228:4, pp. 317-328.

Hartranft, T.H. et al. "Evaluating Surgical Residents Quickly and Easily Against the Milestones Using Electronic Formative Feedback", 2017, J. Surg. Ed., 74:2, pp. 237-242.

Hashimoto, D.A. et al. "See More, Do More, Teach More: Surgical Resident Autonomy and the Transition to Independent Practice", 2016, Acad. Med., 91:6, pp. 757-760.

Hoffman, M.D. et al. "The No-U-Turn sampler: adaptively setting path lengths in Hamiltonian Monte Carlo", 2014, J. Mach. Learn. Res., 15:1, pp. 1593-1623.

Jarman, B.T. et al. "Enhancing Confidence in Graduating General Surgery Residents", 2018, J. Surg. Educ., 75:4, pp. 888-894.

Johnson, C.M. et al. "Can Prospective Usability Evaluation Predict Data Errors?", 2010, AMIA 2010 Annual Symposium Proceedings, pp. 346-350.

Kalet, A. et al. "To fail is human: remediating remediation in medical education", 2017, Perspect. Med. Educ., 6:6, pp. 418-424.

Karim, A.S. et al. "Quality of Operative Performance Feedback Given to Thoracic Surgery Residents Using an App-Based System", 2017, J. Surg. Educ., 74:6, pp. e81-e87.

Kim, S.C. et al. "Cadaver-Based Simulation Increases Resident Confidence, Initial Exposure to Fundamental Techniques", 2016, J. Surg. Educ., 73:6, pp. e33-e41.

Larson, J.L. et al. "Feasibility, reliability and validity of an operative performance rating system for evaluating surgery residents", 2005, Surgery, 138:4, pp. 640-649.

Lesch, H. et al. "VR simulation leads to enhanced procedural confidence in surgical trainees", 2020, J. Surg. Educ., 77:1, pp. 213-218.

Luc, J.G.Y. et al. "Active Learning in Medical Education: Application to the Training of Surgeons", 2016, J. Med. Educ. Curric. Dev., 3, pp. 51-56.

Macewan, M.J. et al. "Continued validation of the O-SCORE (Ottawa Surgical Competency Operating Room Evaluation)", 2016, Teach. Learn. Med., 28(1), pp. 71-79.

"Mastery of Breast Surgery, the American Society of Breast Surgeons", Retrieved on Apr. 25, 2020, Retrieved from the Internet: <https://masterybreastsurgeons.org>.

Mattar, S.G. et al. "General surgery residency inadequately prepares trainees for fellowship", 2013, Ann. Surg., 258:3, pp. 440-449.

McManus, I.C. et al. "Assessment of examiner leniency and stringency ('hawk-dove effect') in the MRCP", 2006, BMC Med. Educ., 6:42, pp. 1-22.

Meholick, A.L. et al. "Use of a Secure Web-Based Data Management Platform to Track Resident Operative Performance", J. Surg Educ., in press, not yet available online.

Nagendran, M. et al. "Virtual reality training for surgical trainees in laparoscopic surgery", 2013, Cochrane Database Syst. Rev., 8:CD006575 pp. 1-37.

Nygaard, R.M. et al. "General surgery resident case logs: do they accurately reflect resident experience?" 2015, J. Surg. Educ., 72:6, pp. e178-e183.

Papanikolaou, I.G. et al. "Changing the way we train surgeons in the 21th century", 2019, Eur. J. Obstet. Gynecol. Reprod. Biol., 235, pp. 13-18.

Quillin, R.C. III, et al. "Operative variability among residents has increased since implementation of the 80-hour workweek", 2016, J. Am. Coll. Surg., 222:6, pp. 1201-1210.

Ratwani, R.M. et al. "Electronic health record usability: analysis of the user-centered design processes", 2015, J. Am. Med. Inform. Assoc., 22:6, pp. 1179-1182.

Roberts, N.K. et al. "Capturing the teachable moment: a grounded theory study of verbal teaching interactions in the operating room", 2012, Surgery, 151:5, pp. 643-650.

Roberts, N.K. et al. "The briefing, intraoperative teaching, debriefing model for teaching in the operating room", 2009, J. Am. Coll. Surg., 208:2, pp. 299-303.

Schwed A.C. et al. "Association of General Surgery Resident Remediation and Program Director Attitudes With Resident Attrition", 2017, JAMA Surg., 152:12, pp. 1134-1140.

Sehli, D.N. et al. "A proposed Resident's operative case tracking and evaluation system", 2016, World Neurosurgery, 87, pp. 548-556.

(56) References Cited

OTHER PUBLICATIONS

Seufert, T.S. et al. "An automated procedure logging system improves resident documentation compliance", 2011, Academic Emergency Medicine, 18, pp. S54-S58.

Shanafelt, T.D. et al. "Relationship between clerical burden and characteristics of the electronic environment with physician burnout" 2016, Mayo Clin. Proc., 91:7, pp. 836-848.

Sittig, D.F. et al. "Defining health information technology-related errors: New developments since to Err is Human", 2011, Archives of Internal Medicine, 171:14, pp. 1281-1284.

Stride, H.P. et al. "Relationship of procedural numbers with meaningful procedural autonomy in general surgery residents", 2018, Surgery, 163:3, pp. 488-494.

Thanawala, R.M. et al. "Novel Educational Information Management Platform Improves the Surgical Skill Evaluation Process", 2018, J. Surg. Educ., 75:6, pp. e204-e211.

Thanawala, R.M. et al. "Education Management Platform Enables Delivery and Comparison of Multiple Evaluation Types" 2019, J. Surg. Educ., 76:6, pp. e209-e216.

Thanawala, R.M. et al. "Inferring Resident Autonomy for Surgical Procedures with Learning Curves", Apr. 30, 2020 poster, Association of Program Directors in Surgery Conference.

Van Heest, A.E. et al. "Resident Surgical Skills Web-Based Evaluation: A Comparison of 2 Assessment Tools", 2019, J. Bone. Joint. Surg. Am., 101:5, pp. e18:1-10.

Wagner, J.P. et al. "Assessment of resident operative performance using a real-time mobile Web system: preparing for the milestone age", 2014, J. Surg. Educ., 71:6, e41-46.

Williams, R.G. et al. "What factors influence attending surgeon decisions about resident autonomy in the operating room?", 2017, Surgery, 162:6, pp. 1314-1319.

Williams, R.G. et al. "Practice Guidelines for Operative Performance Assessments", 2016, Ann. Surg., 264:6, pp. 934-948.

Williams, R.G. et al. "How Many Observations are Needed to Assess a Surgical Trainee's State of Operative Competency?", 2019, Ann Surg., 269:2, pp. 377-382.

Williams, R.G. et al. "A template for reliable assessment of resident operative performance: assessment intervals, numbers of cases and raters" 2012, Surgery, 152, pp. 517-524.

Wohaibi, E.M. et al. "A new web-based operative skills assessment tool effectively tracks progression in surgical resident performance" 2007, J. Surg. Educ., 64:6, pp. 333-341.

Yeo, H. et al. "Attitudes, training experiences, and professional expectations of US general surgery residents: a national survey", 2009, JAMA, 302:12, pp. 1301-1308.

\* cited by examiner

Case Details: [Log] [Eval] [Edit]
Time, Procedures, Patient
Staff

FIG. 3

DATA MANAGEMENT SYSTEM FOR TRACKING AND OPTIMIZING MEDICAL CLINICAL PERFORMANCE

CROSS-REFERENCE TO RELATED APPLICATIONS

This application claims priority to U.S. Provisional Application No. 62/836,792, filed Apr. 22, 2019, the teachings and specification of which is incorporated herein by reference in its entirety.

FIELD OF THE INVENTION

The present invention relates to a web-based platform for tracking medical clinical assignments, such as surgical resident operative assignments, and for linking embedded evaluation instruments to procedure type. The object of this tracking and linking to evaluation instruments is to optimize and improve medical clinical training and performance evaluation for healthcare professionals. The invention provides methods and systems for improving or optimizing performance tracking of a medical professional.

BACKGROUND OF THE INVENTION

Aggregation of clinical and surgical education data is essential for individual trainees, residency programs, education policy makers, and quality-improvement initiatives. However, such data are typically siloed, difficult to access, and burdensome to integrate with other information.

Most medical, clinical, educational, and research initiatives can be greatly facilitated by convenient access to relevant, high-quality data. However, medical and research data are notoriously difficult to access, aggregate, and standardize, especially in a HIPAA-compliant manner. Additionally, hospital staff time constraints and data-entry burnout can easily stymie any new data collection efforts. These issues are further compounded by the complexity of sharing data across institutions.

For example, the American Board of Surgery expects surgical residents to be proficient, safe, and autonomous across 132 "Core" surgical procedures in order to graduate and become practicing surgeons. For surgical educators, it can be a daunting task to solicit and assimilate performance feedback across a program's residents, especially in a timely, comprehensive, and quantitative manner. The situation is similar across other fields of medicine, and not only for surgical and other residents, but also for interns, medical students, nurses, technicians, and other healthcare professionals.

Doctors that are completing their interning and medical residency requirements undergo rigorous and demanding training to become proficient in their chosen field of specialization. A general surgery residency in the United States is currently five years. Specialization in a surgical specialty will add on additional years of training. For example, to specialize in thoracic surgery requires an additional two years of residency. Despite the rigors of such training, some residents may not be receiving the hands-on surgical experiences, training, mentoring, feedback, and any interventional or remedial actions in a timely manner. Part of the reason for this lack of training and feedback is that the procedures for inputting and documenting resident performance information is time consuming and inefficient, which can result in the information not being timely or adequately documented. This situation with information that is not timely or adequately input can lead to residents not knowing where they stand in terms of their training requirements and their performance of medical procedures. Also, performance feedback information that is not timely or adequately input can be detrimental to the learning and performance of a resident. Therefore, the present system for training surgical residents is not fully designed to track and optimize resident performance, which can result in a proportion of residents not being able to successfully complete their residency. Although these shortcomings of residency training are described with a focus on surgical residencies, these shortcomings are common to residencies in other areas of medicine. Additionally, these shortcomings are also found across other areas of medical training including internships, nurse training programs, physician assistant programs, and other professional areas for technicians such as for inhalation therapy and for the operation of specialized diagnostic equipment.

With the current pedagogical model for physician training, objective and timely performance evaluation information about how well trained and proficient a doctor, such as a surgeon, is with performing a specific medical procedure can be lacking. For surgical training in residency, the Accreditation Council for Graduate Medical Education (ACGME) does not attempt to measure when a resident is "ready" to graduate, but instead has a minimum number of cases that the resident is required to perform to meet the accreditation standards. It has been published that most surgery residents report that they do not feel adequately prepared to practice when they graduate from their residency, and that each resident needs a different number of cases in order to become proficient in performing doing a procedure. See, Yeo, Heather, et al. "Attitudes, training experiences, and professional expectations of US general surgery residents: a national survey." Jama 302.12 (2009): 1301-1308; Stride, Herbert P., et al. "Relationship of procedural numbers with meaningful procedural autonomy in general surgery residents." Surgery 163.3 (2018): 488-494; Abbott, Kenneth L., et al. "Number of Operative Performance Ratings Needed to Reliably Assess the Difficulty of Surgical Procedures." Journal of surgical education 76.6 (2019): e189-e192; and Williams, Reed G., et al. "How many observations are needed to assess a surgical trainee's state of operative competency?" Annals of surgery 269.2 (2019): 377-382.

Also, educational quality varies across institutions. Some institutions allow residents to dig in and get hands-on experience doing procedures early in their career, whereas other institutions require residents for the first year or two to only stand to the side of the operating table to observe the procedure over the surgeon's shoulders. Further complicating physician training and competency evaluation is that the standard way for assessing physician expertise and competency is from the physician's patient outcomes over a significant period of time—this can often be years. It is well known that outcomes depend on other factors, such as the underlying health of the patient, level and quality of postoperative care, insurance reimbursement, etc. Because of these other factors, it is difficult to determine which portion of the outcome is directly attributable to a single doctor.

To address the forgoing shortcomings, we have therefore developed a Bayesian learning curve model for building a method and data management system for the tracking and optimization of medical clinical performance for healthcare professionals, and in particular for medical residents such as surgical residents. This model is the basis of our platform for medical scoring and profiling. The methods and systems of the present invention intelligently aggregate and anonymize large volumes of data, and can optimize data-entry workflows to make new data collection efforts feasible, thereby facilitating training and optimizing performance for healthcare professionals. Furthermore, the information is input and organized to facilitate the operation and efficiency of the computer and data storage systems.

SUMMARY OF THE INVENTION

The present invention relates to platform, such as a web-based platform, to track resident operative assignments and to link embedded evaluation instruments to procedure type. The present invention provides an improvement upon conventional methods and systems for tracking and evaluating resident performance and provides an important training tool for advancing resident knowledge and skill development.

Additionally, these methods and systems are contemplated as being applicable across other areas across the medical profession and include internships, nurse training programs, physician assistant programs, and other professional areas for technicians such as for inhalation therapy and for the operation of specialized diagnostic equipment The present invention includes, among others, the following embodiments.

A method for improving or optimizing performance tracking or monitoring of a healthcare professional comprising the steps of:

a) collecting (clinical) performance evaluations from a group of supervisory healthcare professionals for the performance of one or more selected tasks (medical procedures) for a peer group of subordinate health professionals;

b) assessing the clinical complexity of each task from step a);

c) compiling and standardizing the evaluations collected from step a) versus predetermined standards for the successful completion of the task;

d) determining the prior distributions for relevant parameters for each supervisory healthcare professional and for each subordinate healthcare professional for each task based on step b) and c);

e) performing a calculation [such as a Markov Chain Monte Carlo (MCMC) statistical sampling method] from the output of step d) to determine the (posterior) distributions of the resultant learning curves for the healthcare professions;

f) from the (posterior) distributions from step e), determining the learning curves for each healthcare professional for each step of the task; and g) comparing the output (learning curve for each healthcare professional) from step f) to that of the peer group to determine the performance and/or proficiency of each health care professional.

A method for [efficiently] accelerating the acquisition of a requisite skill level for a healthcare professional.

A method for [efficiently] accelerating the acquisition of a requisite skill level for a healthcare professional comprising the steps of:

a) acquiring data of a preselected set of tasks, a list of completed tasks (progress) for a healthcare professional, and evaluations of task performance for the healthcare professional;

b) comparing the acquired data to preselected set of standards to rank the healthcare professional (student) versus the standards; and c) presenting a suggested next task to be performed to efficiently acquire the requisite skill level.

A method for statistically modelling a healthcare professional's progress in acquiring a requisite skill level.

A method for statistically modeling a healthcare professional's progress comprising the steps of;

i) collecting (clinical) performance evaluations from a group of supervisory healthcare professionals for the performance of one or more selected tasks (medical procedures) for a peer group of subordinate health professionals;

ii) assessing the clinical complexity of each task from step i);

iii) compiling and standardizing the evaluations collected from step i) versus predetermined standards for the successful completion of the task;

iv) determining the prior distributions for relevant parameters for each supervisory healthcare professional and for each subordinate healthcare professional for each task based on step ii) and iii);

v) performing a calculation [such as a Markov Chain Monte Carlo (MCMC) statistical sampling method] from the output of step iv) to determine the (posterior) distributions of the resultant learning curves for the healthcare professions;

vi) from the (posterior) distributions from step v), determining the learning curves for each healthcare professional for each step of the task; and vii) comparing the output (learning curve for each healthcare professional) from step vi) to that of the peer group to determine the performance and/or proficiency of each health care professional.

A method for quantifying the learning rate of the healthcare professional.

A method for quantifying the clinical learning rates and clinical autonomy levels for healthcare professionals, comprising the steps of:

a) gathering performance evaluations along with the relevant clinical encounter details for the healthcare professional for each medical task, b) estimating the complexity or difficulty of each clinical encounter for each medical task for which evaluations are gathered from step b), c) estimating the grader bias of each evaluator for each evaluation, d) estimating the healthcare professional's current clinical autonomy level, e) estimating the learning rate, such as the healthcare provider's longitudinal improvement in clinical autonomy per clinical encounter for each medical task, and f) estimating the maximum clinical autonomy for the healthcare professional as the maximum autonomy level after a sufficient number of clinical encounters for the medical task to thereby provide the quantitation.

A method for predicting task (case, medical procedure) volume according to the present invention.

A method according to the present invention that is HIPPA (Health Insurance Portability and Accountability) Act compliant.

A method wherein the healthcare professional is selected from the group consisting of medical students, interns, residents, fellows, doctors, physician assistants, nurses, nurses' aides, and medical technicians.

A method involving a teaching or evaluation situation, including a supervisory healthcare professional (e.g. an attending surgeon) and a subordinate healthcare professional (e.g. a surgical resident).

A system for performing or implementing the methods of the present invention comprising a computer, a server or data storage system, a user interface, a non-transitory computer readable medium storing computer program instructions, software for analyzing the input data and providing an output, and a data array.

A system comprising:
a) an automated data entry component for entering data in a clinical setting,
b) an advanced statistical modeling component to quantify the healthcare professional's competence or expertise with a medical procedure;
c) a component to index, match, and through machine learning or artificial intelligence provide an output of educational content for the healthcare professional based on the professional's clinical schedule, specialty, current level of training, and level of expertise; and
d) a component to characterize the clinical experience and performance of a group of healthcare professionals for normalizing the expertise level of each healthcare professional that of the healthcare professional's matched peers.

A system wherein the user interface is selected from the group consisting of a graphical user interface (GUI), a command-line interface, or a menu driven interface.

A system wherein the user interface is a graphical user interface (GUI).

A GUI for augmenting a clinical schedule with case-based actions, comprising:
a) an element showing staff assignments for each clinical encounter, and
b) an element juxtaposed to each assignment clinical details, showing buttons, tags, status labels, or actionable links for encounter-related activities, such as case logging, performance evaluations, data quality control, and availability of medical educational content.

A method for improving performance efficiency of a healthcare professional comprising the steps of:
a) compiling medical data selected from healthcare personnel task completion data and task performance evaluation data for a group of healthcare professionals;
b) segregating and correlating the data by each professional for the group;
comparing the data versus preselected standards to rank order each professional versus the standards;
d) using the data from step (c) to provide an evaluation for each healthcare professional.

A user interface for augmenting a clinical schedule with case-based actions, comprising:
a) an element showing staff assignments for each clinical encounter, and
b) juxtaposed to the clinical details, showing buttons, tags, status labels, or actionable links for encounter-related activities, such as case logging, performance evaluations, data quality control, and availability of medical educational content.

A method for quantifying the clinical learning rates and clinical autonomy levels for medical learners, comprising the steps of:
a) gathering performance evaluations along with the relevant clinical encounter details,
b) estimating the complexity or difficulty of each clinical encounter for which evaluations are performed,
c) estimating the grader bias of each evaluator,
d) estimating the learner's current clinical autonomy level,
e) estimating the learning rate: the learner's longitudinal improvement in clinical autonomy per clinical encounter, and
f) estimating the maximum clinical autonomy: the learner's maximum autonomy level after a large number of clinical encounters, to thereby provide the quantitation.

A method for indexing and selecting procedural codes for case logging comprising the steps of:
a) collecting and curating sets of procedural codes,
b) matching codes to medical and clinical concepts,
c) matching scheduled clinical encounters and procedures to medical and clinical concepts,
d) profiling the medical expertise and educational needs of the case staff member,
e) training a decision aid to matching cases with appropriate codes, based on medical concept match and previous logging patterns, and
f) presenting the appropriate codes to the user as suggestions and search results for case logging, to thereby provide the indexing and selection.

A method for combining evaluations with case logging, in order to provide incentives for users to complete evaluations, comprising the steps of:
a) profiling the medical expertise and educational needs of the teaching faculty member,
b) profiling the medical expertise and educational needs of the medical learner,
c) matching the appropriate evaluations to clinical encounters and teaching experiences, and
d) presenting the evaluations to the teaching faculty member for the teaching clinical encounter, to provide the incentive.

A method for pairing a clinical schedule with case logging, to track logging progress and compliance, comprising the steps of:
a) matching the clinical encounters from clinical schedules to a case logging system, based on clinical details, case identifiers, and patient identifiers,
b) identifying the log status of each clinical encounter,
c) showing the case log status to the clinical staff member, and
d) calculating the logging compliance of each relevant clinical staff member, to thereby provide the pairing.

A method of pairing a clinical schedule with performance evaluations, to track evaluation progress and compliance, comprising the steps of:
a) matching clinical encounters from clinical schedules to an evaluation system or evaluation log, based on clinical staff member information, clinical details, case identifiers, and patient identifiers,
b) identifying the evaluation status of each teaching clinical encounter,
c) showing the evaluation status to the teaching faculty member, and
d) calculating the evaluation compliance of each teaching faculty member, to thereby provide the pairing.

A method for suggesting (identifying) medical staff members for case assignments, based on the expertise and educational requirements of each staff member, comprising the steps of:
a) compiling a list or data bank of clinical staff members who are available for cases,
b) profiling the medical expertise and educational needs of each staff member,
c) matching staff members to cases, based on schedule availability, domain expertise, clinical details, and educational requirements such as minimum required cases for educational programs, and d) showing the appropriate staff members for the case, as suggestions or search results for case assignments, to thereby provide the identification.

A computer system for teaching faculty to remotely conduct coaching sessions for oral board preparation via phone, video conference/video chat, or session videos, comprising:

a) a component for facilitating the scheduling of coaching sessions and choice of appropriate coaching partners, by presenting lists of optional coaching partners and learners, b) a component for enabling the coaching sessions via a computer or phone, and c) a component for providing a history of previous coaching sessions to the teaching faculty member and to the learner.

A method of pairing teaching faculty to residents and fellows, to optimize the teaching experience, comprising the steps of:

a) profiling the medical, clinical, and scientific expertise of each teaching faculty member, b) profiling the medical, clinical, scientific expertise, and educational requirements of each clinical learner, and c) matching the teaching faculty to the learners, based on schedule availability, medical topic preference, and relevant previous test scores, to thereby provide the pairing.

A method for matching clinical schedules to appropriate educational content, based on the expertise and educational requirements of the medical learner, comprising the steps of:

a) profiling the medical, clinical, and scientific expertise of each learner in a department, b) aggregating medical educational content, such as journal articles, textbooks and chapters, demonstration videos, procedural and anatomical illustrations, operational guides, etc., c) profiling the medical subject of each educational content item, by identifying and indexing the item by the relevant medical concept terms, d) matching content items that are appropriate to clinicians for their clinical encounters, based on the medical concepts described in the items, the recommendations by clinicians and their domains of expertise, the medical concepts and procedures appropriate to the clinician's clinical encounters, the degree of expertise/autonomy and educational needs of the clinician, e. delivering the targeted content to the clinicians to help them prepare for their upcoming clinical encounters, and f) enabling the clinician to provide feedback on the quality and appropriateness of the suggested content, in order to further train the matching engine, and to provide the clinician with a convenient list of liked items.

A method for inferring the effect of clinical simulation training and experience on clinical performance and outcomes, and prescribing targeted simulation exercises for educational development, comprising the steps of:

a) aggregating previous historical data for procedural simulation exercises and clinical learners' scores, b) tracking clinical performance evaluations, along with clinical outcomes, for learners, c) using statistical models to estimate the clinical autonomy and performance level of each learner, d) using medical and procedural concepts to match clinical activities to relevant types of simulation exercises, e) tracking the change of the learner's clinical performance with the frequency and quality of clinical experience and simulation exercises, f) using statistical models to infer the effect of simulation training on clinical performance and autonomy for each learner, g) identifying situations where a learner would benefit from simulation exercise training, and prescribing the appropriate exercises to the learner, and h) providing an analytics dashboard to the clinical educators, to enable guided oversight into simulation experiences and adjustments to clinical educational strategies.

A method for predicting case volume for medical learners, based on clinical schedules and previous case experience per department, comprising the steps of:

a) aggregating historical data on case logs, clinical schedules, and service rotation schedules for learners in a clinical education program, b) using statistical models to approximate the expected number, rate, and types of clinical encounters for each service rotation or period within the clinical education program, c) profiling a clinical learner's current level of clinical performance and autonomy, using performance evaluations and statistical modeling, d) using statistical models to project the expected number, rate, and types of clinical encounters that the learner is likely to experience during future periods of the education program, and e) based on these models' results, creating projections and alerts for learners and their teaching faculty, helping learners understand their relative standing in performance compared to their peers, and helping educators rank their learners and receive notifications when any learners could benefit from early remediation.

These and other aspects of the present invention will become apparent from the disclosure herein.

BRIEF DESCRIPTION OF THE DRAWINGS

FIG. 3 is an illustration of a user interface, such as a graphical user interface (GUI), where the case logging and evaluations are integrated into the resident's schedule.

FIG. 20A shows the histogram of the time that attendings spent in completing resident performance evaluations (the majority less than 20 seconds). FIG. 20B shows the histogram the lag time, the number of days that attendings waited after a teaching case until they submitted their resident performance evaluations (the majority in less than one week FIGS. 21A and 21B show that the platform evaluations arrived earlier.

FIG. 24A shows the data for attending surgeons and FIG. 24B shows the data for residents, in each plot showing number of cases versus time.

FIG. 25A shows total resident case volume. FIG. 25B shows the case volume for an individual resident.

DETAILED DESCRIPTION OF THE INVENTION

Figure 1:
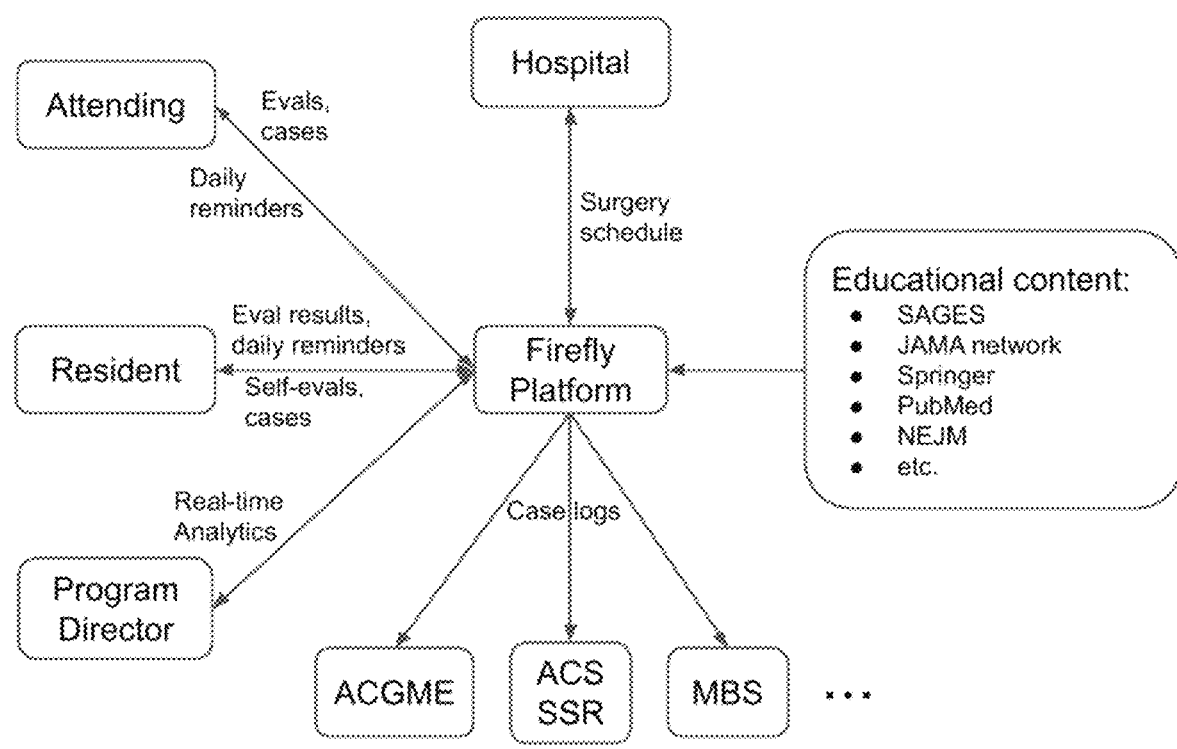
FIG. 1 is an illustration of how the platform of the present invention connects multiple systems and users.

We built a HIPAA-compliant, web-based platform for comprehensive management of surgical research and resident education information, including operative schedules, procedural details and codes, clinical outcomes, resident and staff case assignments, performance evaluations, surgical simulation exercises, and aggregated analytics. HIPPA is an abbreviation for the Health Insurance Portability and Accountability Act of 1996, which stipulates how Personally Identifiable Information such as Protected Health Information (PHI), maintained by the healthcare and healthcare insurance industries should be protected from fraud and theft. The platform is designed to synchronize with operating room schedules and populates case logs across resident and attending case-logging databases. The platform automatically juxtaposes operating room cases with multiple types of evaluations, and matches cases with relevant educational content, for example surgical videos, journal articles, anatomical illustrations, etc. for resident preparedness. Patient-identifying data are protected and removed from analysis wherever possible.

At the start of each research project, custom data integrations and smart data curation tools are constructed to facilitate data aggregation and standardization of data structures. Wherever manual data entry is required, the platform uses an artificial intelligence layer to automate as much of the data-entry process as possible, with smart predictive suggestions and auto-completion of forms, trained by reinforcement learning from previous data entry patterns. Resident performance evaluations are used to fit Bayesian learning curve models, to measure operative autonomy for each resident for each case type. A self-service research portal is also contemplated as part of the system, where investigators can browse posted research projects to join, or they can create their own and invite others to collaborate. The platform anonymizes and standardizes data for sharing across institutions and can be deployed multi-institutionally.

The comprehensive data platform enables near real-time monitoring and detailed analyses of operative activity and performance, and facilitates research collaboration and data collection. Potential benefits include use in tailoring curricula, and large-scale program improvement, and remediation of doctor performance.

The HIPAA-compliant web-based platform is used to track resident operative assignments and to link embedded evaluation instruments to procedure type. The platform delivered multiple evaluation types, including Ottawa O-Score autonomy evaluations. Autonomy scores are gathered across teaching faculty and combined with the residents' history of case assignments. For this analysis we focused on cholecystectomy cases. The data were entered into a Bayesian logistic learning curve model, including estimates for the resident's learning lag (the number of cases needed until rapid learning), the maximum learning rate, and the autonomy limit (the maximum autonomy level we expect the resident to achieve after a large number of cases). The learning curve model included an ordinal response component, which inferred the resident's actual autonomy level from the faculty's ordinal Likert-scale ratings. It also inferred the faculty's implicit "hawk or dove" grader bias (i.e. graders who consistently graded lower or higher, respectively, than the average), while accounting for reported case complexity. The model was applied to each resident across the program, creating a learning baseline against which each individual resident can be compared to his or her peers.

We have therefore developed a Bayesian learning curve model (a model based on the probability of an event occurring, based on prior knowledge of conditions related to the event) that incorporates surgical case history along with Likert-scale and Zwisch-scale [not the only evaluation scale] evaluation data to infer and quantify resident operative autonomy. The Likert-scale is five- or seven-point rating scale which is used to allow an individual to express how much they agree or disagree with a particular statement. The Zwisch-scale, as shown in Table 1, is a rating scale that includes anchoring behaviors and cues to advancement for residents in surgical training. The Zwisch scale is just one example of an evaluative rating scale that can be used as part of the present invention. Other rating scales can be employed, including one specifically developed for the present invention as further described below and in Table 2.

The Zwisch scale was designed to guide faculty to develop graduated autonomy for their learners during training and acts as an assessment tool, allowing faculty to understand where each trainee stands in their progression towards independence, and provides teaching strategies to help them progress. This framework is based on the "Zwisch" scale, a conceptual model that was originally used by Joseph Zwischenberger, MD, FACS, a thoracic surgeon and the chair of the department of surgery at the University of Kentucky. See, DaRosa D A, Zwischenberger J B, Meyerson S L, et al. A Theory-Based Model for Teaching and Assessing Residents in the Operating Room. JSE. 2013; 70:24-30. This model has been refined over the past several years, and now consists of four levels named "Show & Tell," "Active Help," "Passive Help," and "Supervision Only." Each level describes the amount of guidance provided by faculty to residents. The Zwisch Scale, as summarized in Table 1, describes the amount of guidance provided by faculty to residents.

TABLE 1

Summary of Zwisch Scale

| Zwisch Scale Level | Attending Behaviors | Resident Behaviors |
| --- | --- | --- |
| Show & Tell | Performs >50% of critical portion; demonstrates key concepts, anatomy, and skills; explains case (narrates) | Opens and closes; observes and listens during critical portion |
| Active Help | Leads the resident (active assist) for >50% of the critical portion; optimizes the field/exposure; demonstrates plane/structure; coaches technical skills; coaches next steps; identifies key anatomy | The above, plus actively assists (i.e. anticipates surgeon's needs); practices component technical skills |
| Passive Help | Follows the lead of the resident (passive assist) for >50% of the critical portion; acts as a capable first assistant; coaches for polish, refinement of skills, and safety | The above, plus can "set up" and accomplish next steps; recognizes critical transition points |
| Supervision Only | Provides no unsolicited advice for >50% of the critical portion; monitors progress and patient safety | The above, plus mimics independence; can work with less experienced assistant; can safely complete case without faculty guidance; recovers from most errors; recognizes when to seek advice/help |

Furthermore, the platform of the present invention has been designed to utilize the following evaluative autonomy scale that we developed and is intended to reflect the degree of independence demonstrated to the faculty surgeon evaluator by the surgical resident. See Table 2.

TABLE 2

Evaluative Autonomy Scale

| Rating | Value | Meaning |
| --- | --- | --- |
| I Did | 1 | I had to do. Resident did not yet have the knowledge or skill to do. Resident requires complete hands on guidance. |
| Steer | 2 | I had to talk them through. Resident is able to perform tasks but requires constant direction. |
| Prompt | 3 | I had to prompt them from time to time. Resident demonstrates some independence, but requires intermittent direction. |
| Backup | 4 | I needed to be in the room just in case. Resident has independence but is unaware of risks and still requires supervision for safe practice. |
| Auto | 5 | I did not need to be there. Resident has complete autonomy and independence, understands risks and performs safely, practice ready. |

The platform provides for comprehensive management of resident education information, including resident operative performance evaluations. To assess evaluation timeliness, we compared the lag time for platform-based evaluations to that of end-of-rotation evaluations. We also assessed evaluation compliance, based on a time threshold of 5 days for platform evaluations and 2 weeks for end-of-rotation evaluations.

Evaluation of performance is an essential responsibility of the teaching faculty members of any surgical residency. Although the Accreditation Council for Graduate Medical Education (ACGME) explicitly defines this responsibility in section V of the Common Program Requirements, specific evaluation instrument types, specific methods to achieve timely completion, control of evaluation quality, and effective use as tools to facilitate positive development are areas where training programs have enormous latitude to utilize innovative methods. The use of evaluation as a feedback tool is vitally important in surgical training, and although published evidence of obstacles to achievement of effective feedback are scant, this issue is nonetheless frequently cited in the context of time pressures and conflicting responsibilities experienced by faculty members. There is agreement that absence of effective feedback is an impediment to high quality medical training, and that frequent evaluations are required for effective resident assessment. See, Anderson P A. Giving feedback on clinical skills: are we starving our young? J Grad Med Educ. 2012; 4:154-158; Williams R G, Verhulst S, Colliver J A, Sanfey H, Chen X, Dunnington G L. A template for reliable assessment of resident operative performance: assessment intervals, numbers of cases and raters. Surgery. 2012; 152: 517-524. https://doi.org/10.1016/j.surg.2012.07.004. discussion 524-7 Epub 2012 Aug. 28; Dougherty P, Kasten S J, Reynolds R K, Prince M E, Lypson M L. Intraoperative assessment of residents. J Grad Med Educ. 2013; 5:333-334. https://doi.org/10.4300/JGME-D-13-00074.1; Williams R G, Swanson D B, Fryer J P, et al. How many observations are needed to assess a surgical trainee's state of operative competency? Ann Surg. 2019; 269:377-382. https://doi.org/10.1097/SLA.0000000000002554; and (5) Fryer J P, Teitelbaum E N, George B C, et al. Effect of ongoing assessment of resident operative autonomy on the operating room environment. J Surg Educ. 2018; 75:333-343. https://doi.org/10.1016/j.jsurg.2016.11.018. Epub 2017 Mar. 28.

Figure 6:
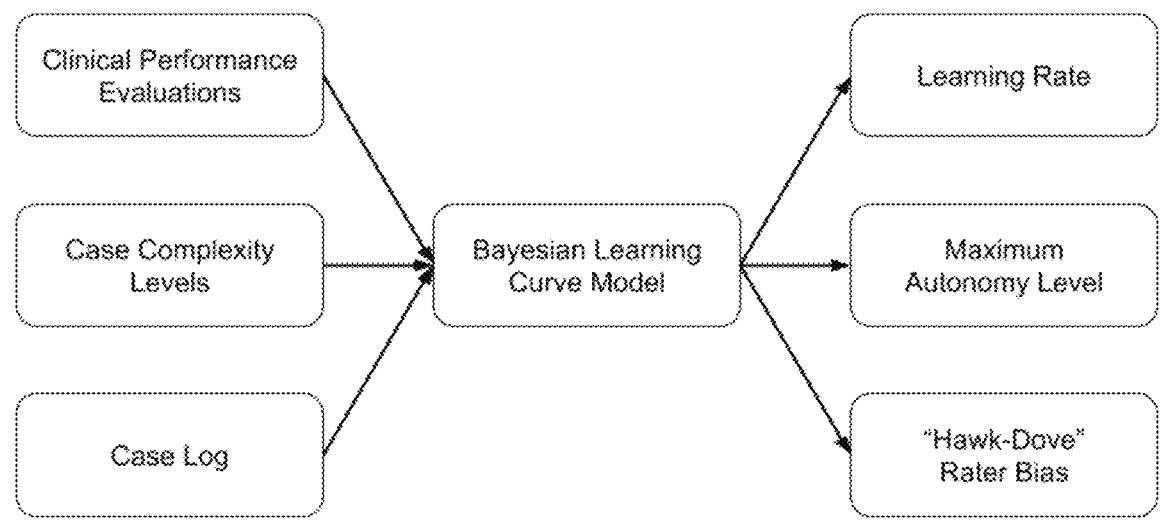
FIG. 6 is a diagram showing the statistical learning curve model of the present invention, to infer the expertise or autonomy level of a doctor for a procedure.
Figure 7:
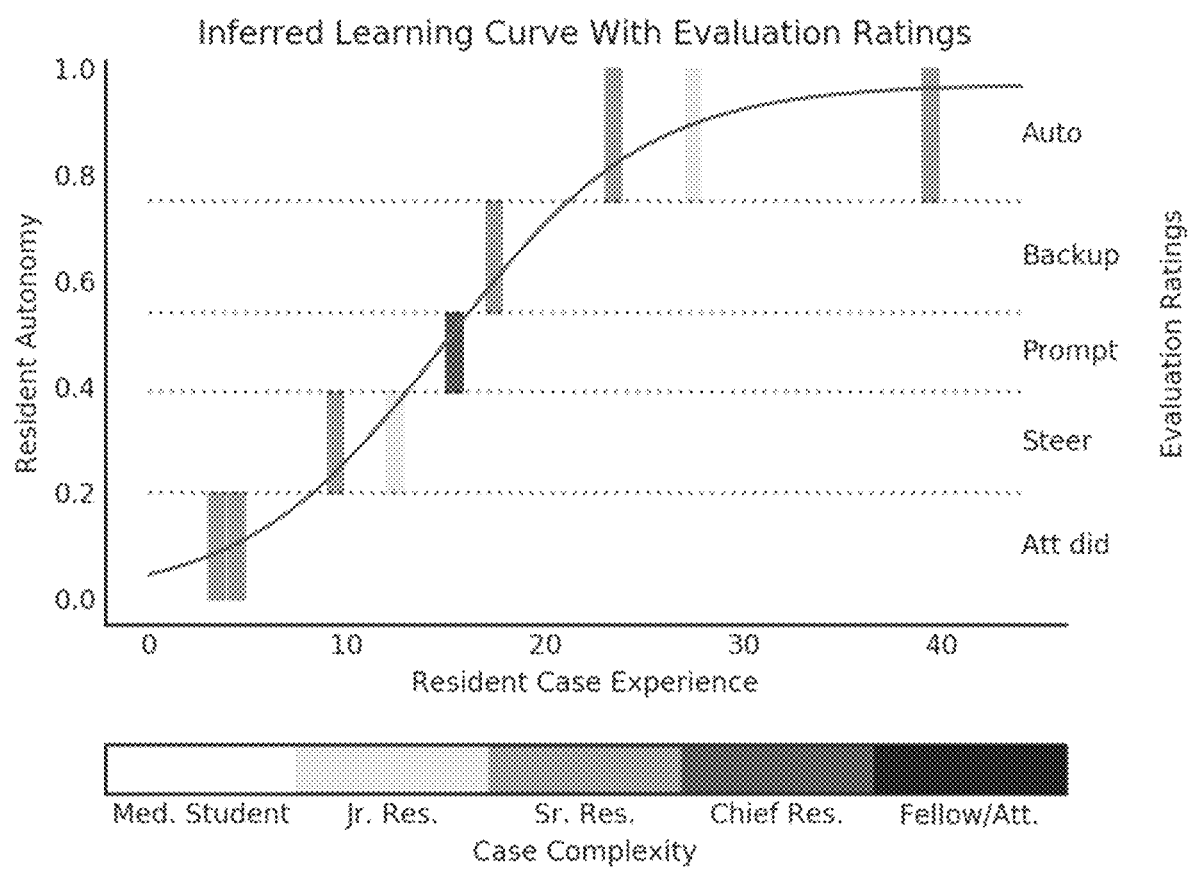
FIG. 7 is a diagram showing the modeling of resident learning and autonomy.
Figure 8:
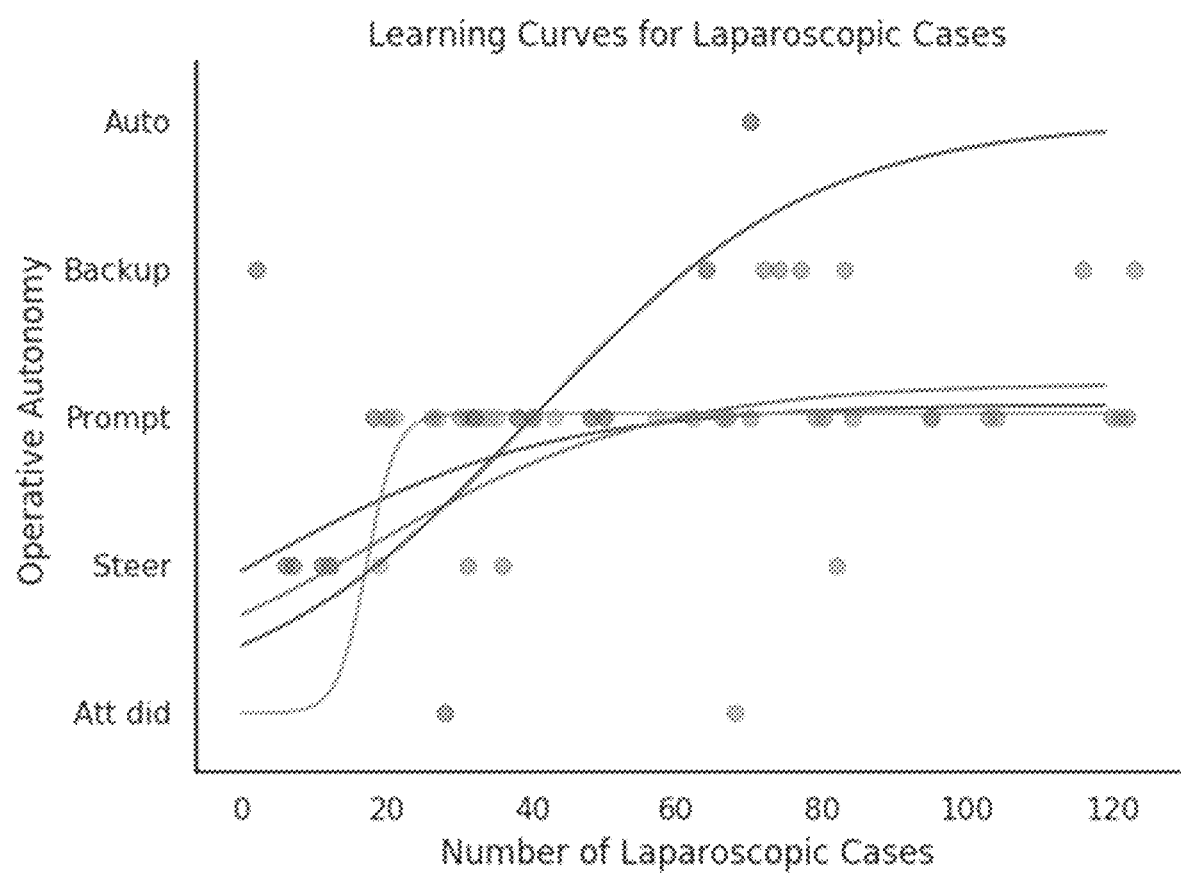
FIG. 8 is a plot showing learning curves for individual residents for laparoscopic cases. This figure illustrates the modeling process where we have plotted the most likely (maximum a posteriori estimate) learning curve for each surgery resident in a small group of residents that were having difficulty learning laparoscopic procedures. Each resident has its own line. The horizontal axis is the number of procedures that the resident performed over time, and the vertical axis is the autonomy score (the higher, the more independent the resident). The dots show some individual evaluations received over time.

FIG. 6 illustrates the flow and logic of the system and methods of the present invention. The data flow and steps can be summarized as follows:

1. Gather the clinical performance evaluations for the doctor we're modeling, as well as for his peers. The evaluations can be of different types. The model can use partial information to infer missing data for each step of clinical procedures.

2. Gather and standardize everyone's case logs (records of a doctor's clinical encounters and procedures).

3. Based on the evaluation and clinical data, estimate the clinical complexity level for each case. The case complexity is important for knowing how informative each case is for estimating the doctor's expertise level. If the case is way too easy or way too hard for the doctor, then it doesn't contribute much to our understanding of the doctor's expertise level.

4. Estimate the prior distributions for relevant model parameters: hawk-dove rater bias (whether the teacher typically gives low or high grades) for each person who completed an evaluation (typically a teaching faculty member), and the doctor's learning rate (how fast the doc learns with each case) and maximum autonomy/expertise level (how independent we predict the doc will be after a large number of cases). Do this for each step of each procedure.

5. Run a Markov Chain Monte Carlo (MCMC) statistical sampling method to estimate the posterior distributions of the learning curve parameters.

6. From the posterior samples, infer the doctor's learning curve for each step of each procedure. The model will generate a distribution for each parameter: the learning rate, max autonomy level, and the hawk-rater biases of each of his teachers. And finally, 7. Compare each doctor to his peers, in order to calculate his rank and percentile during the learning process. This will show us whether the doctor is ahead or behind his peers in his learning process.

The performance advantages and features of the present invention include: Automated data entry and efficient workflow in a clinical setting.

Advanced statistical modeling system to quantify a medical provider's competence or expertise with a medical procedure.

A system to index, match, and suggest educational content for medical provider based on his clinical/surgical schedule, specialty, and current level of training & expertise. And also, A system to characterize the clinical/surgical experience and performance of a group of medical professionals, and to normalize the expertise level of each professional according to that of his/her matched peers.

Figure 2:
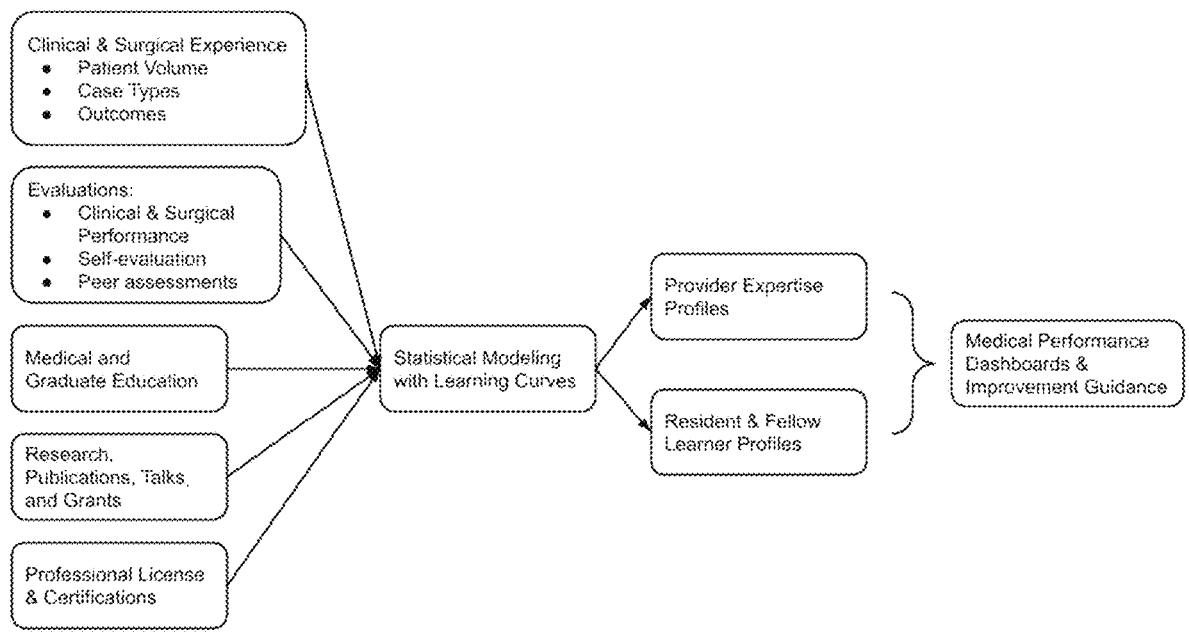
FIG. 2 is a diagram for the scoring and profiling system for medical providers and learners, showing the input data and output profiles.

FIG. 2 shows the data flow and processing system for quantifying medical expertise and constructing medical learner profiles. The data flow and steps can be summarized as follows:

1. For each medical provider, gather clinical and surgical experience, including patient volume, case types with procedure information, and patient outcomes.

2. Gather evaluation data, including evaluations of clinical and surgical performance, self-evaluations, and peer assessments.

3. In addition to clinical information, also gather available data on medical and graduate education, research outcomes (e.g. publications, posters, conference talks, and grants), and professional licenses and certifications.

4. Perform the statistical modeling and construction of learning curves on each relevant medical task and procedure, as described above.

5. From these learning curves, construct medical expertise profiles and learner profiles, to summarize each provider's expertise levels and to compare to relevant peer groups.

6. Assemble the expertise and learning profiles into a live dashboard for tracking clinical activities and learning rates. From the Firefly (the present invention) targeted education system, include targeted educational content, learning milestones, and suggestions, as appropriate for each medical learner.

The platform combined disparate data across 37 institutions, comprising 47 surgical departments and 100 surgical services, aggregating 278,410 surgical operative cases with 340,128 associated procedures, and 493,807 case assignments. From these, 184,318 resident cases were logged with the ACGME, and 17,969 cases were logged to the American College of Surgeon's (ACS) Surgeon Specific Registry. The platform helped the teaching faculty submit 4,285 resident operative performance evaluations, enabling the construction of 165 procedure-specific learner profiles. Additionally, the platform aggregated 54,126 data points from resident surgical simulation exercises, including virtual reality laparoscopic simulations.

The systems and methods of the present invention provide advantages over those currently available and include the following:

The invention uses statistical models to infer a medical practitioner's ability and to project the learning and ability in the future as the practitioner gains more clinical experience.

The invention uses statistical models to account for confounders, such as the evaluator's "hawk vs dove" bias and the clinical case complexity.

The invention is flexible and can use many types of evaluations, rather than requiring a defined evaluation type up front.

The invention can be used to create scores and profiles for medical expertise and autonomy, which can be used in a variety of ways. Also, the platform and evaluations are not dependent on predefined job goals.

Additionally, the following features describe the methods and systems of the present invention.

The present invention automates medical chores such as surgical data chores. The features provide for: scheduling and quickly assigning cases; automated case logging into the databases for the ACGME, the American College of Surgeons (ACS), etc.; quick evaluations for early, useful doctor feedback; live analytics for improvement tracking; and curated educational content to facilitate case preparation. These foregoing features result in saved time, particularly for case logging alone.

The platform connects multiple systems and uses, as is exemplified in FIG. 1. FIG. 1 shows the platform's data integration and user role architecture. The important components can be summarized as follows:

1. The Firefly platform connects with the hospital's data system to access relevant clinical data and schedules, for example the operative schedule for a surgery team.

2. The platform connects with, indexes, and profiles large amounts of educational content, for example journal articles, anatomy diagrams, and medical procedure videos. The Firefly targeted education system associates each piece of content with relevant medical activities, using techniques including machine learning and natural language processing.

3. The platform connects with case logging systems for automated storage and reconciling of a provider's clinical experience. The Firefly case reconciling system performs data curation and automatically identifies and merges duplicate case records.

4. The platform searches and assembles relevant information for various types of users, including a comprehensive real-time dashboard of clinical and educational information for a residency program director, medical tasks and evaluations for residents, and medical tasks and evaluations for attendings.

Other features of the method and platform include: evaluations and learning profiles, targeted education, case logging, and case analytics.

There is a requirement for individual residents and programs. See Nygaard, Rachel M., Samuel R. Daly, and Joan M. Van Camp. "General surgery resident case logs: do they accurately reflect resident experience?" Journal of surgical education 72.6 (2015): e178-e183, which notes a 24.2% discrepancy between cases log into ACGME and cases residents participated in based on electronic medical records (EMR). The most common reason for this discrepancy is that 9.6% "forgot to log", which highlights inconsistent logging practices amongst residents. On the other hand, it has been shown that semi-automation of procedure logging in emergency medicine leads to 168% increase in procedure logging. See, Seufert, Thomas S., et al. "An automated procedure logging system improves resident documentation compliance." Academic Emergency Medicine 18 (2011): S54-S58.

Also, contemplated with the present invention ae the computer systems, associated hardware, servers, software, code, and algorithms necessary for compiling storing, analyzing, and manipulating the inputted information, as well as conducting the various searches, projections, simulations, and outputs. As illustrated in FIG. 3, which shows an example of a user interface for the methods and systems of the present invention, the case logging and evaluations are integrated into the schedule via a user interface. The user interface can be a graphical user interface (GUI). As is well known, a GUI is a type of user interface that allows users to interact with electronic devices. The interface can provide for graphical icons and audio indicators such as a primary notation, instead of text-based user interfaces, typed command labels or text navigation. In other embodiments of the present invention, the interface can be a command-line interface or a menu driven interface. There is quick case logging with smart Common Procedural Technology (CPT) suggestions. CPT is a formal way of assigning codes to medical procedures, and is commonly done for billing, as insurance companies have predetermined amounts they reimburse for each code. These codes are useful for case logging, for the doctor to be more precise about the procedures performed.

Figure 5:
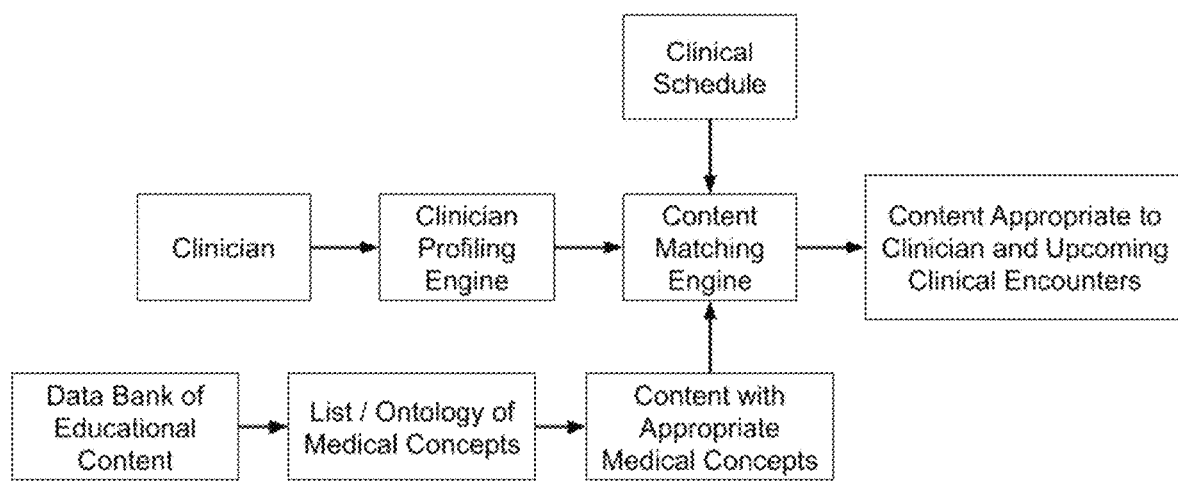
FIG. 5 is a diagram showing the data flow and processing for the content matching engine to identify and rank order smart suggestions and smart search for targeted educational material and exercises for a medical practitioner.
Figure 22:
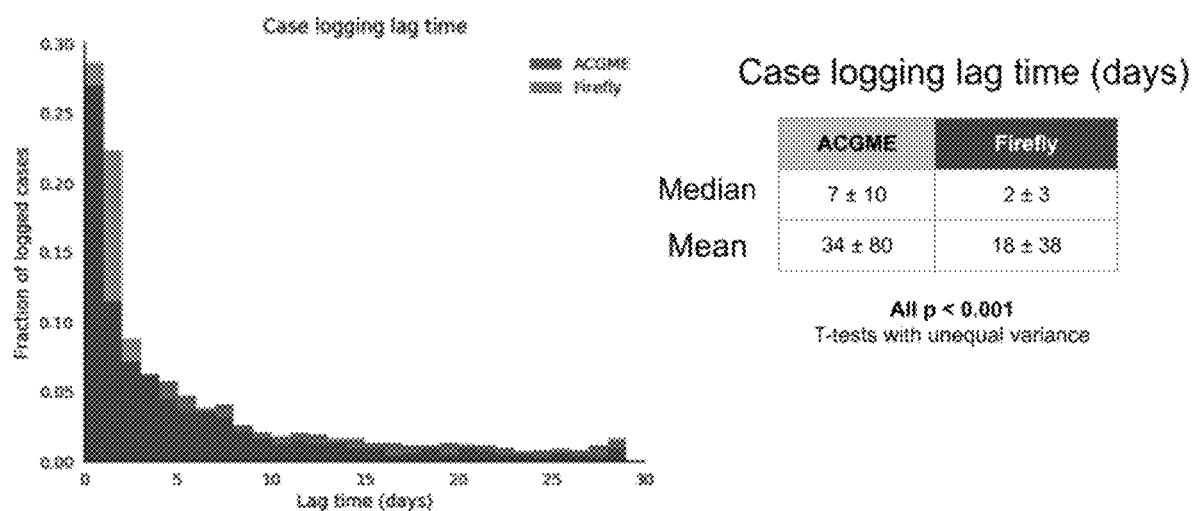
FIG. 22 is a plot of the fraction of lagged cases versus the lag time (in days) showing a statistical difference that residents log earlier into the system of the present invention versus the ACGME database.
Figure 23:
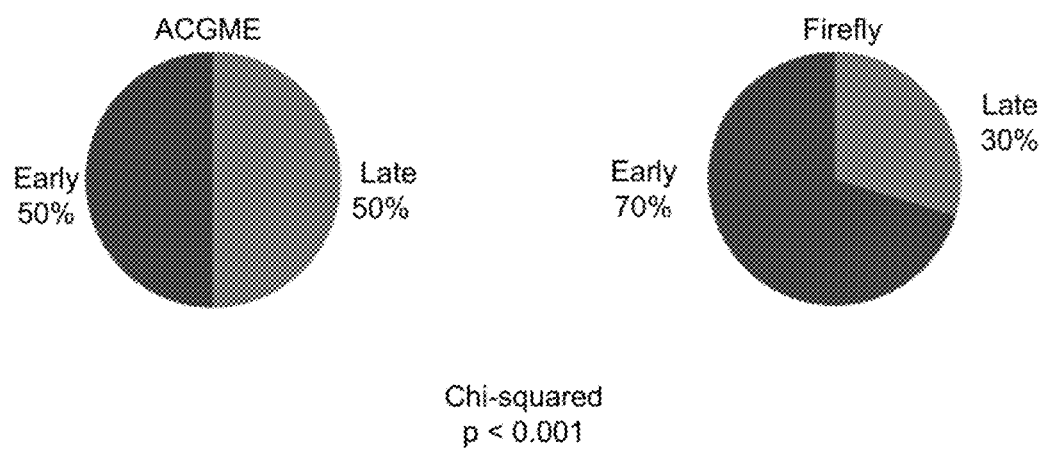
FIG. 23 shows the logging behavior of early versus late logging for the system of the present invention versus the ACGME database.
Figure 24A:
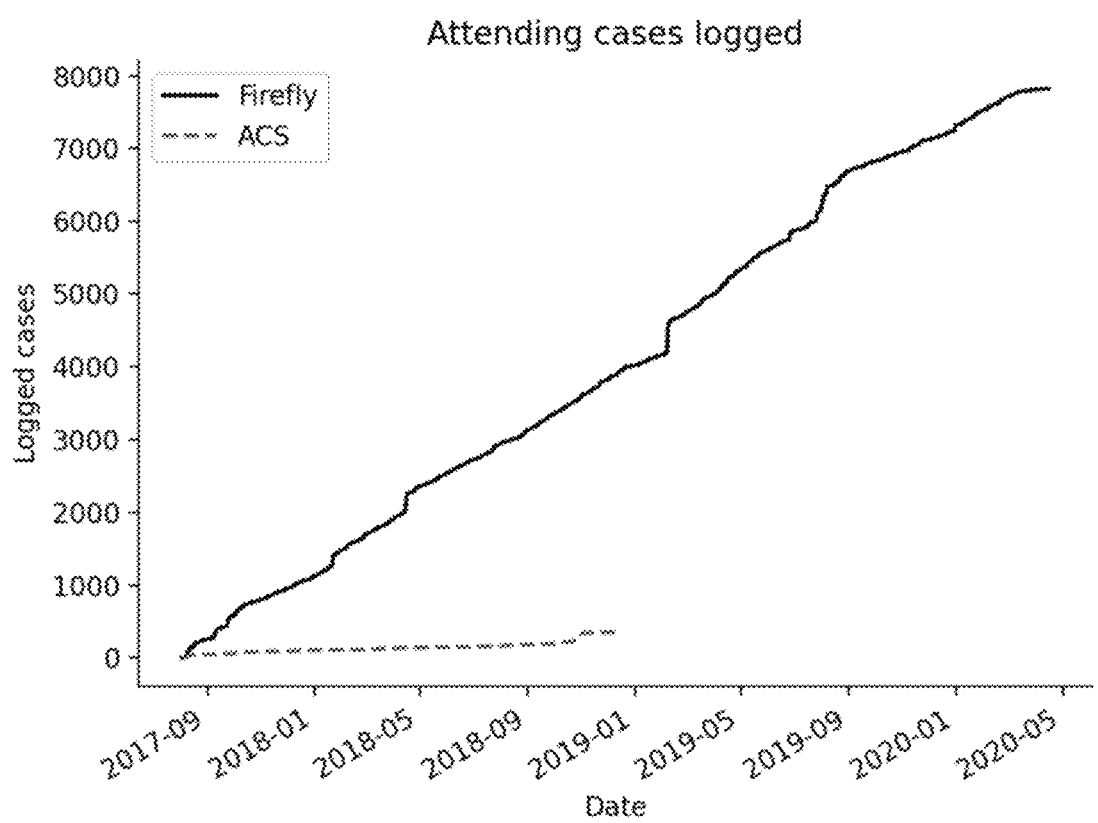
FIGS. 24A and 24B show plots demonstrating that surgeons prefer the logging system of the present invention (i.e. Firefly, i.e. the present invention) versus the ACS database.
Figure 24B:
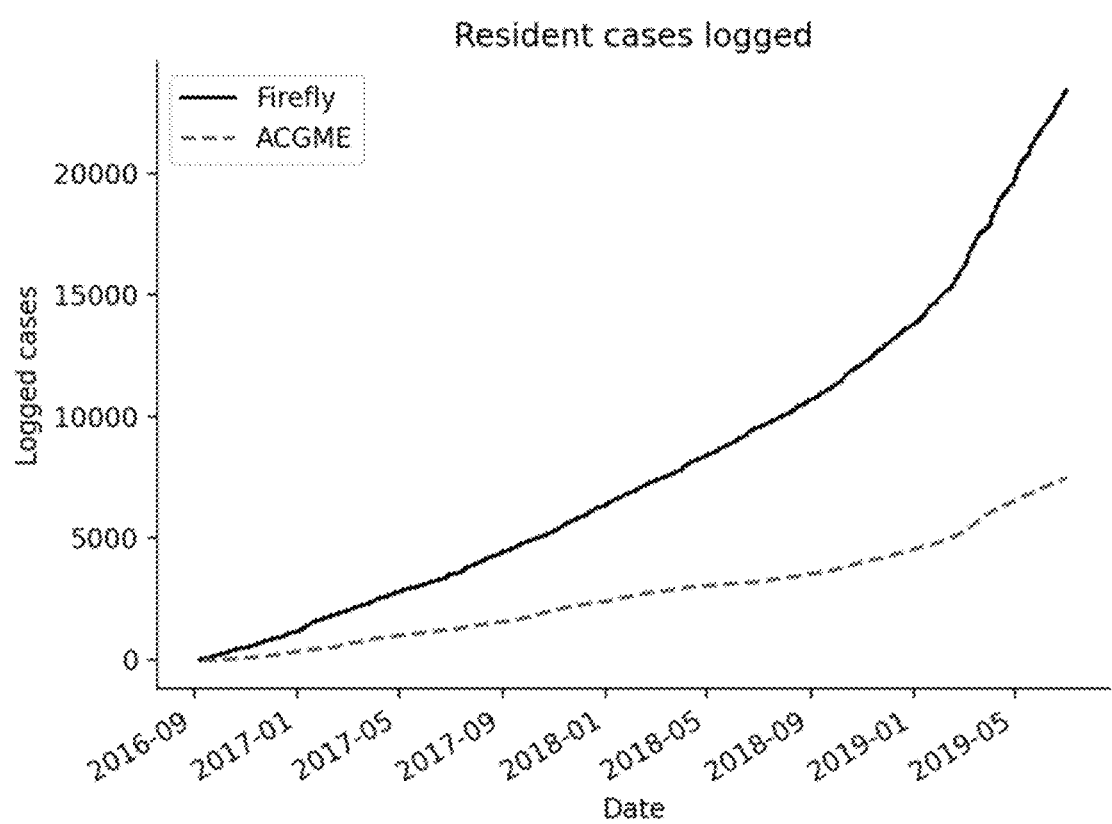
Figure 25A:
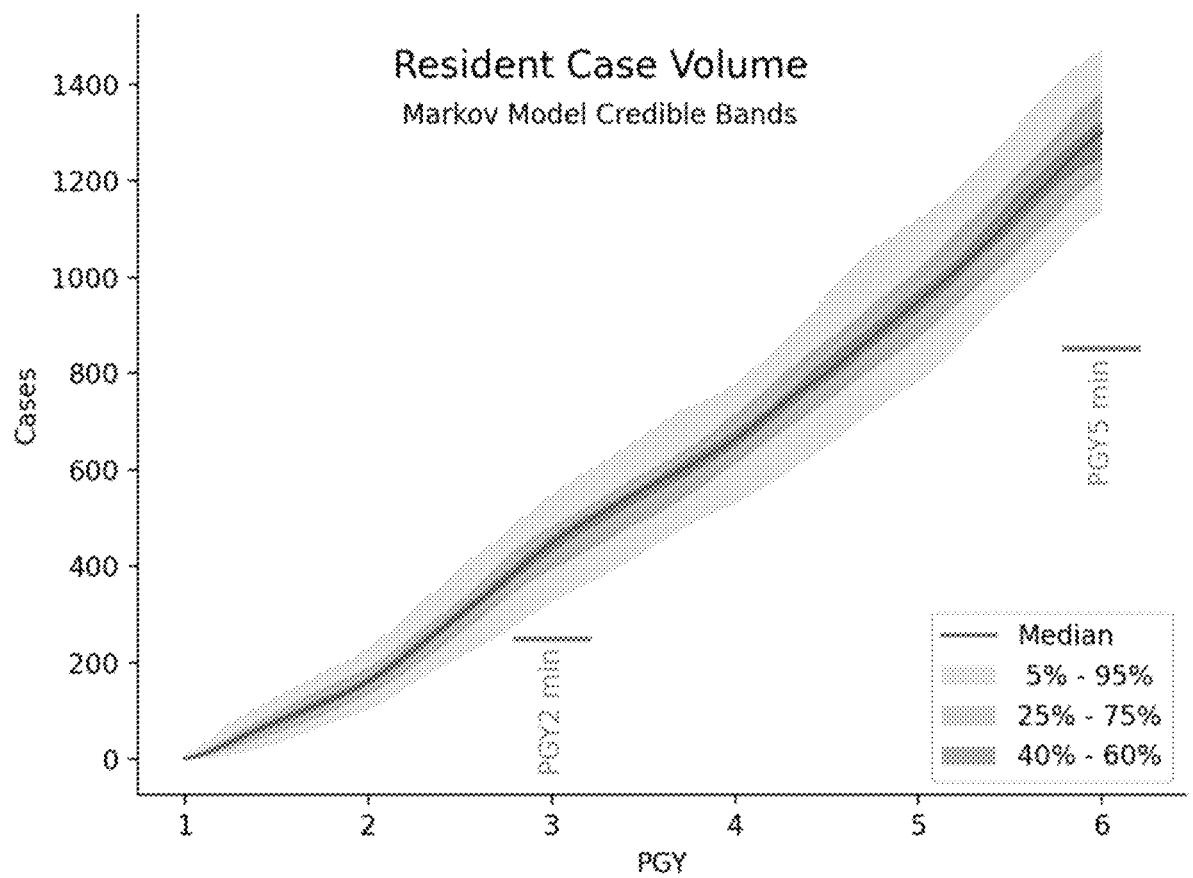
FIGS. 25A and 25B are plots showing how the methods and systems of the present invention are useful for predicting case volume.
Figure 25B:
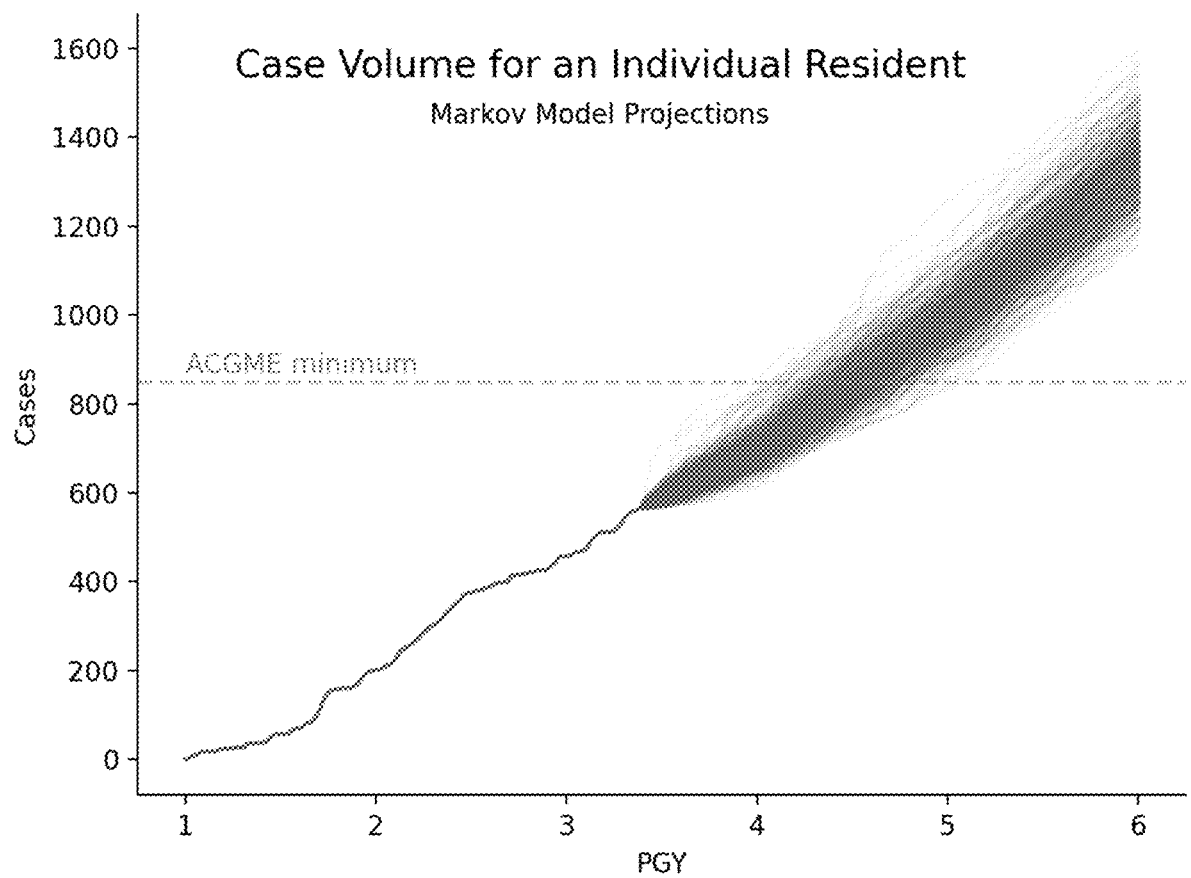

The systems and methods allow for bidirectional syncing with ACGME and ACS case logs and automatically fills in case details from the schedule, using machine learning to search and suggest CPT codes. The system also has the capability to learn from case logging patterns across a department. Advantages include: the rapid smart adding of cases such that the surgeons log their cases very quickly (10 seconds) and without delay (the same day). We have demonstrated that residents log their cases earlier (more than 5 days earlier) than into ACGME. See FIG. 22. Also, there is an advantage of early logging behavior for the platform versus ACGME database. See FIG. 23. We also have found that there is a preference amongst surgeons to use the system of the present invention versus ACGME. See FIGS. 24A and 24B5. These are plots showing that surgeons prefer the logging system of the present invention (i.e. Firefly) versus the ACS database. FIG. 24A shows the data for attending surgeons and FIG. 24B shows the data for residents, in each plot showing number of cases versus time The systems and methods of the present invention provide for a live analytics dashboard which can be synchronized with ACGME reports. This feature allows residents to explore and compare case mix. There is also the capability to compare case experience across residents. The benefit of these features is the ability to predict resident case volume. See FIGS. 25A and 25B which illustrate how the methods and systems of the present invention are useful for predicting case volume. FIG. 25A shows total resident case volume. FIG. 25B shows the case volume for an individual resident.

Yet another feature is the ability to have multiple evaluations delivered on a desktop and phone.

Figure 12:
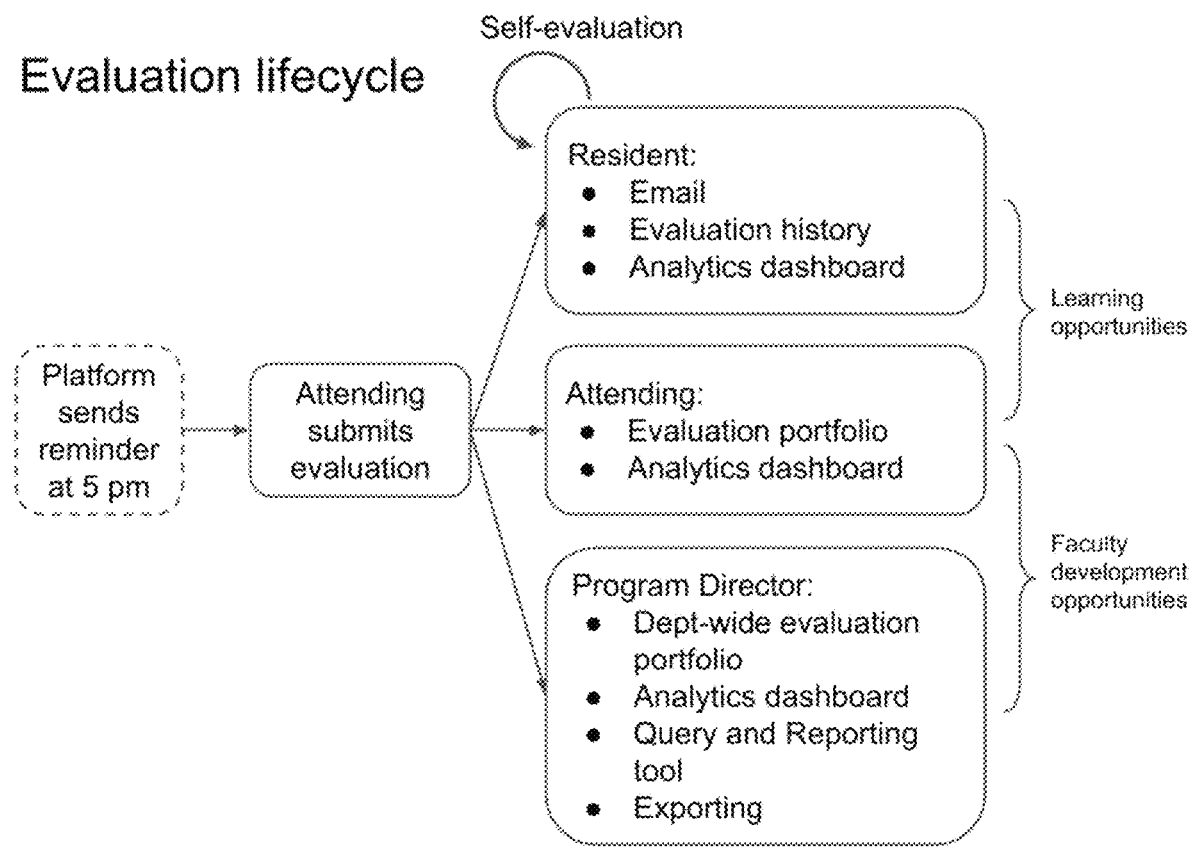
FIG. 12 is a diagram showing the evaluation lifecycle captured by the system and methods of the present invention.

FIG. 12 shows the evaluation life cycle diagram for the methods and systems of the present invention. Either at the end of each teaching case or at the end of the workday (depending on the user's notification preferences), the platform sends an evaluation request to the teaching attending. Once the attending then completes and submits the evaluation, the platform sends the evaluation to provide the resident with immediate performance feedback. The evaluation is also inserted into the attending's personal evaluation portfolio and dashboard, as well as the program director's department-wide evaluation portfolio and analytics dashboard. This dashboard provides a live view of all evaluation activity across the department, along with data query and exploration tools for visualizing and analyzing the data.

Figures 20A, 20B:
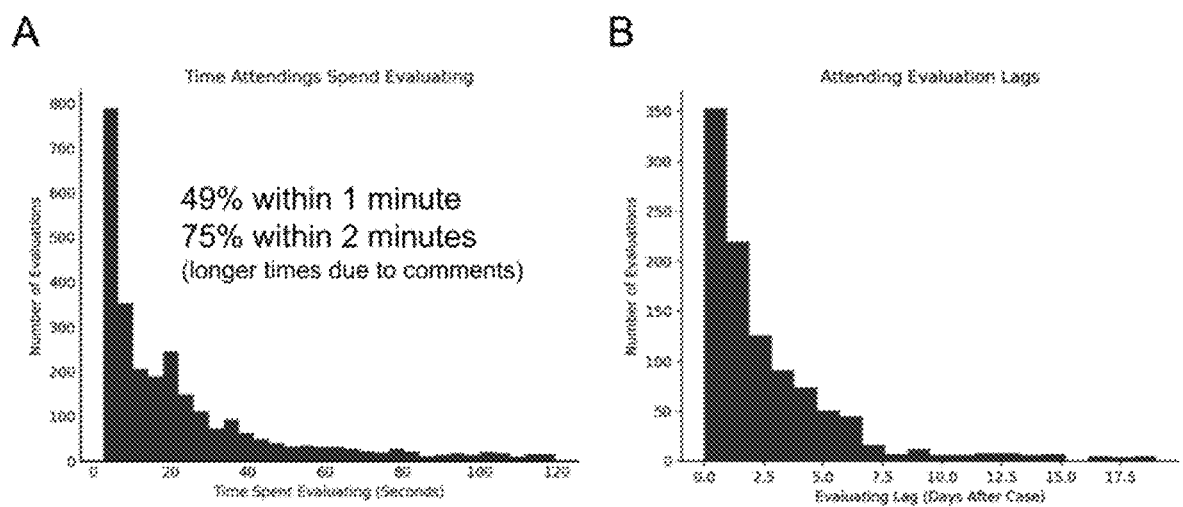
FIGS. 20A and 20B show that attending surgeons evaluate quickly and without delay.
Figure 21A:
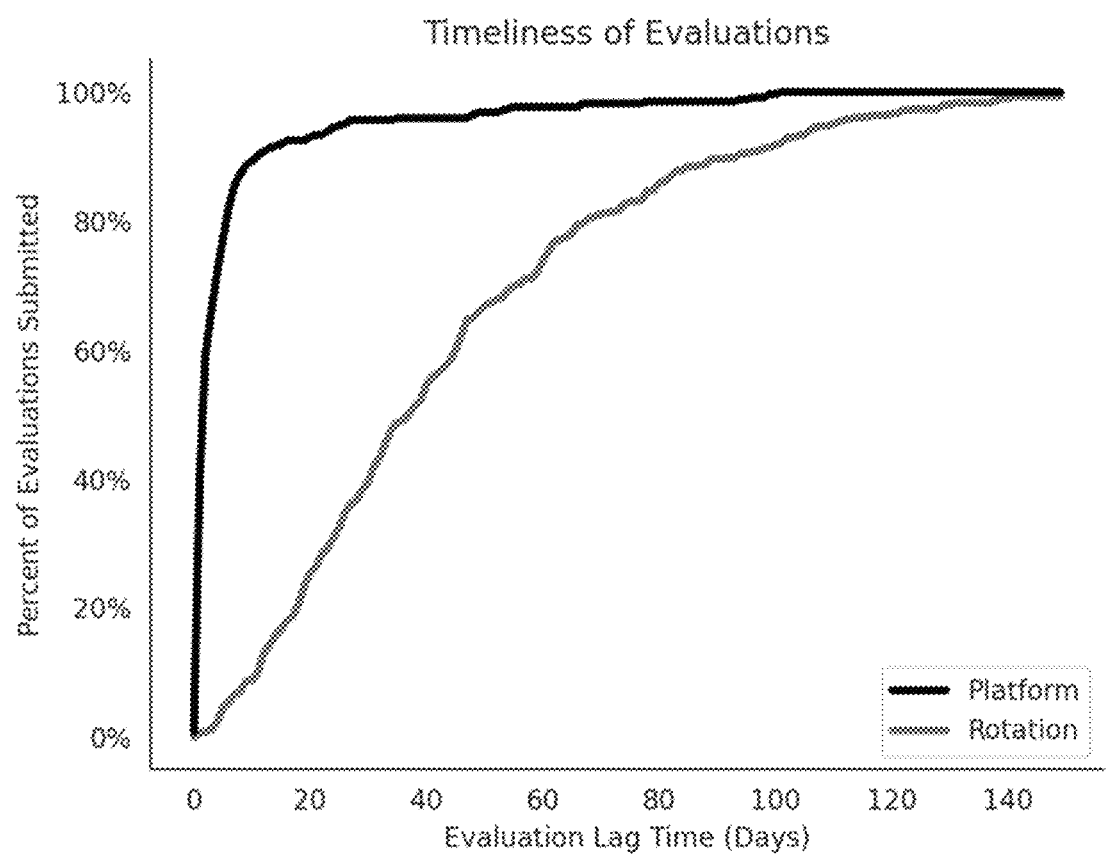
FIG. 21A shows a plot illustrating the percent of evaluations submitted over time, showing that evaluations were submitted much earlier via the Firefly platform (i.e. the present invention) than the end-of-rotation evaluations.
Figure 21B:
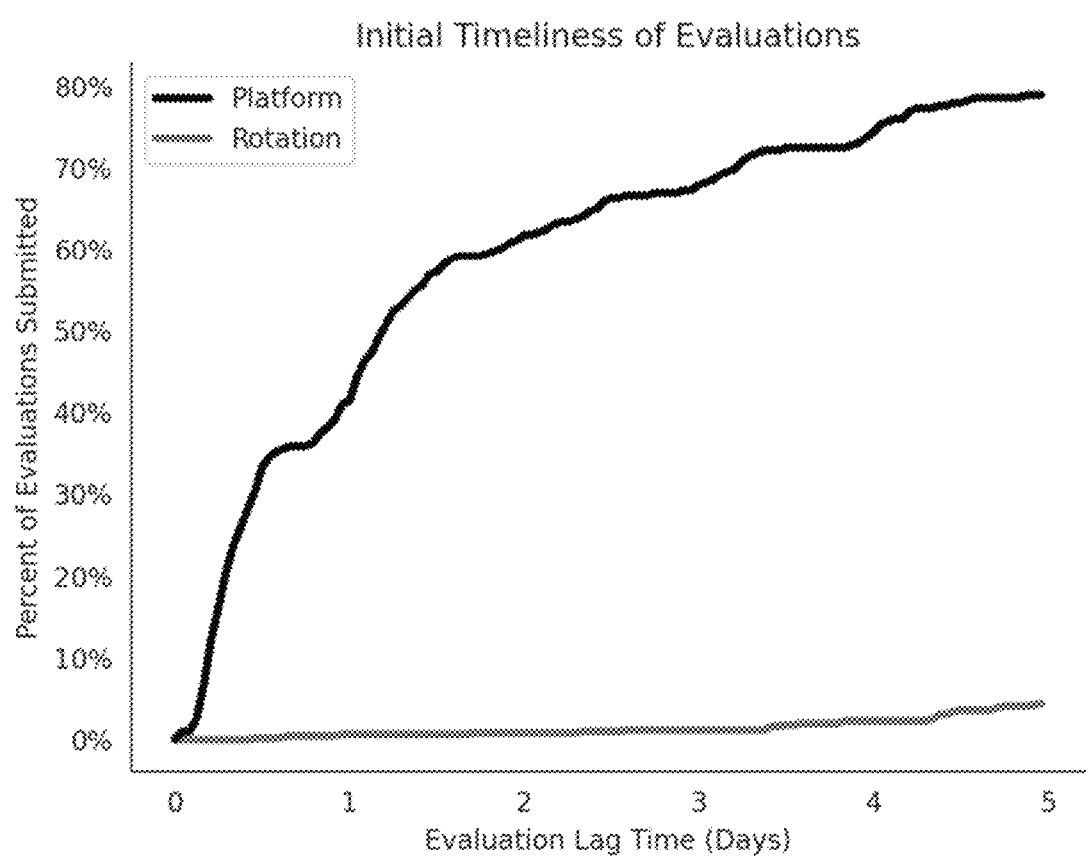
FIG. 21B shows a detailed view of evaluations submitted within the first 5 days, when 80% of evaluations are submitted via the Firefly platform, but very few end-of-rotation evaluations are submitted.

The methods and systems of the present invention provide advantages for resident evaluation. The attending surgeons evaluate quickly and without delay. This enables residents to get feedback early, when it is most helpful and relevant throughout their rotations. See FIGS. 20A and 20B show the timeframes in which attendings complete their resident performance evaluations. Facilitated by the platform, attendings typically complete their evaluations within one minute (FIG. 5-24 A). Because the process is quick, attendings submit their evaluations within a few days of the case, rather than postponing the task (FIG. 5-24 B). Also, the attending surgeons evaluate quickly for multiple evaluation types. We have demonstrated that platform evaluations arrived 35 days earlier. See FIGS. 21A and 21B. Because the Firefly platform provides convenient prompts and reminders for the evaluations, as well as optimized workflow to make the evaluation process quick, the attendings complete their evaluations over a month earlier on the platform than they had traditionally done without it (FIG. 21A). On Firefly, approximately 95% of the evaluations were submitted within a few days of each teaching case (FIG. 21B).

The analytics dashboard can show live evaluation statistics, resident learning trends, and even has the ability to show a system-level view of evaluations across a department.

Other features of the systems and methods of the present invention include the capability for modeling for resident learning and autonomy. See FIG. 7. This shows the resident autonomy level using the evaluation scale of Table 2 on the y-axis versus case complexity on the x-axis. The level of the doctor is also shown, i.e. medical student, junior resident, senior resident, chief resident, and fellow/attending surgeon. There is the capability for self-assembling consensus evaluations, links to educational content from the schedules, a targeted education library of curated content, and an active research feature with a content recommendation engine.

Data Security and HIPPA Compliance and Protected Health Information (PHI).

The systems and methods of the present invention having the important advantage of being HIPPA compliant. The invention utilizes strong encryption for all data connections and the databases and can be securely hosted on the could. The invention allows for two-factor authentication with routine penetration testing and risk assessments on data system infrastructure. A department administrator can be assigned to manage users and data access. Also, any PHI can be optional on the platform.

The system can be securely protected from the provider and utilizes blind storage for encrypted PHI where it cannot decrypt or read surgeon-encrypted data, because the PHI is encrypted locally on the surgeon's computer with secret encryption keys. To decrypt data, potential hackers would have to break into the system provider and hospital data systems simultaneously.

Also, the system has a very tight IT footprint. By default, the system operates independently without any IT support or data integration burden from the hospital. The system optionally can accept a secure data feed of the surgical schedule, which saves the surgeons from having to type in their case information for case logging.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1

Educational Information Management Platform Improves the Surgical Resident Evaluation Process.

Objective:

We sought to increase compliance and timeliness of surgery resident operative evaluation, by providing faculty and residents with a platform linking evaluation to analytics and machine-learning-facilitated case logging. See, Thanawala, R., Jesneck, J. and Seymour, N. E., 2018. Novel Educational Information Management Platform Improves the Surgical Skill Evaluation Process of Surgical Residents. Journal of Surgical Education, 75(6), pp. e204-e211.

Design:

We built a HIPAA-compliant web-based platform for comprehensive management of resident education information, including resident operative performance evaluations. To assess evaluation timeliness, we compared the lag time for platform-based evaluations to that of end-of-rotation evaluations. We also assessed evaluation compliance, based on a time threshold of 5 days for platform evaluations and 2 weeks for end-of-rotation evaluations.

Participants:

23 attendings and 43 residents for the platform cohort. 15 services and 45 residents for the end-of-rotation cohort.

The desired outcome of surgical education is the achievement of defined competencies including the ability to function with a high degree of autonomy in the operating room. It is critically important to evaluate operative performance in effective ways in order to make well informed statements on this (1). Evaluations are most effective when they are completed and made available to the learner without delay (2,3). However, completing individual evaluations in the desired time frame requires frequent data entry and places a time and work burden on surgical educators (4,5). Large clinical productivity expectations, burdensome non-clinical workloads, and the risk of burnout that accompanies ever-increasing demands for time that is in short supply are threats to the quality of educational activities such as resident performance evaluations. Other forms of practice data entry can also be affected (6,7), including keeping up with required clerical tasks and records of operative cases (8,9).

Several strategies have been used to ease the process of operative evaluations, including mobile applications (10), web-based applications (11-13), and residency information management systems. These innovations might improve the process of evaluation submission in their specific niches, but demonstration of this is challenging. We sought to address the evaluation submission process with an additional strategy that centralizes data entry in a comprehensive platform, where an evaluation is accessed along with other tasks that utilize some of the same data stream. Combining related tasks into one workflow increases ease of use and avoids the cognitive burden of navigating to isolated systems in a more complicated workflow (6). Such a comprehensive system can take advantage of experience in other established data-intensive fields, such as engineering and computer science, to optimize workflow, improve usability, decrease cognitive burden of frequent tasks, and create positive feedback loops for beneficial user habits (8). It was our aim to add value to the process of surgical skills evaluation by providing faculty and resident participants in the evaluation process a platform linking evaluation to case logging, and thereby improving compliance, timeliness, and sustainability of evaluation practice.

Material and Methods

We built a HIPAA-compliant web-based platform for comprehensive management of resident education information including performance evaluations. To optimize evaluation workflow, the platform synced with the institution's operating room (OR) schedules and automatically merged patient and case data, including coding description of operative procedures, attending surgeon, resident surgeon, date of operation, and OR location. These combined data were delivered in real-time in an editable system that included case schedule pertinent to the user, specific resident case assignments, case logging functionality for residents and attendings, and finally, resident operative performance evaluations (FIG. 1). Case logging workflow benefited from using the scheduled case information to limit manual data entry. Case information was validated (or edited) following a case when the platform was accessed. Logging data were then automatically inserted into the Accreditation Council for Graduate Medical Education (ACGME) case log for residents and the American College of Surgeons-Surgeon Specific Registry (ACS-SSR) for attendings. Additionally, the platform learned from previous case logging patterns to provide smart search and automated suggestions for Current Procedural Terminology (CPT) codes (14) using machine learning. For each operation with a resident, the platform offered to the attending a resident operative performance evaluation with a single mouse click or screen tap. Evaluations consisted of a slightly modified Ottawa O-Score instrument rating of operative autonomy on a five-point Likert scale for 12 items along with the option to insert narrative comments (15). Evaluation results were displayed in a real-time analytics dashboard for the evaluating attendings, evaluated residents, and program director. For ease of use, the platform was mobile friendly, so that attendings could complete evaluations from their smartphones. The platform automatically sent attendings daily reminder emails to complete evaluations, and upon completion it immediately pushed evaluation results to the residents. The real-time evaluation status was embedded into the surgical schedule beside each case, facilitating rapid progress through multiple evaluations, and reminding evaluators to complete all evaluations.

Timeliness of evaluation submission was used as the principal measure of the platform's usability. Understanding that broader evaluations of resident performance on individual rotations was a different construct, we did compare timeliness of platform-based evaluations with end-of-rotation evaluations delivered to evaluators via the Program's overall information management package (New Innovations, Uniontown, Ohio) (16). For the platform, we measured timeliness by the lag in number of days between the operation and the evaluation submission. For end-of-rotation evaluations, timeliness was the lag in number of days between the end of rotation and the evaluation submission. We compared median lag times using Mood's median test (17), and compared mean lag times using unpaired t-test with unequal variance (18). Using these lag values, we applied thresholds to define evaluation compliance. We defined compliance for the platform evaluations as within five days of the case and for the end-of-rotation evaluations as within two weeks of the end of rotation. We compared compliance rates and tested for statistical significance by using bootstrap sampling. We also recorded the hour of day when attendings submitted their evaluations, in order to understand how the evaluation process fit into their daily workflow.

Figure 14:
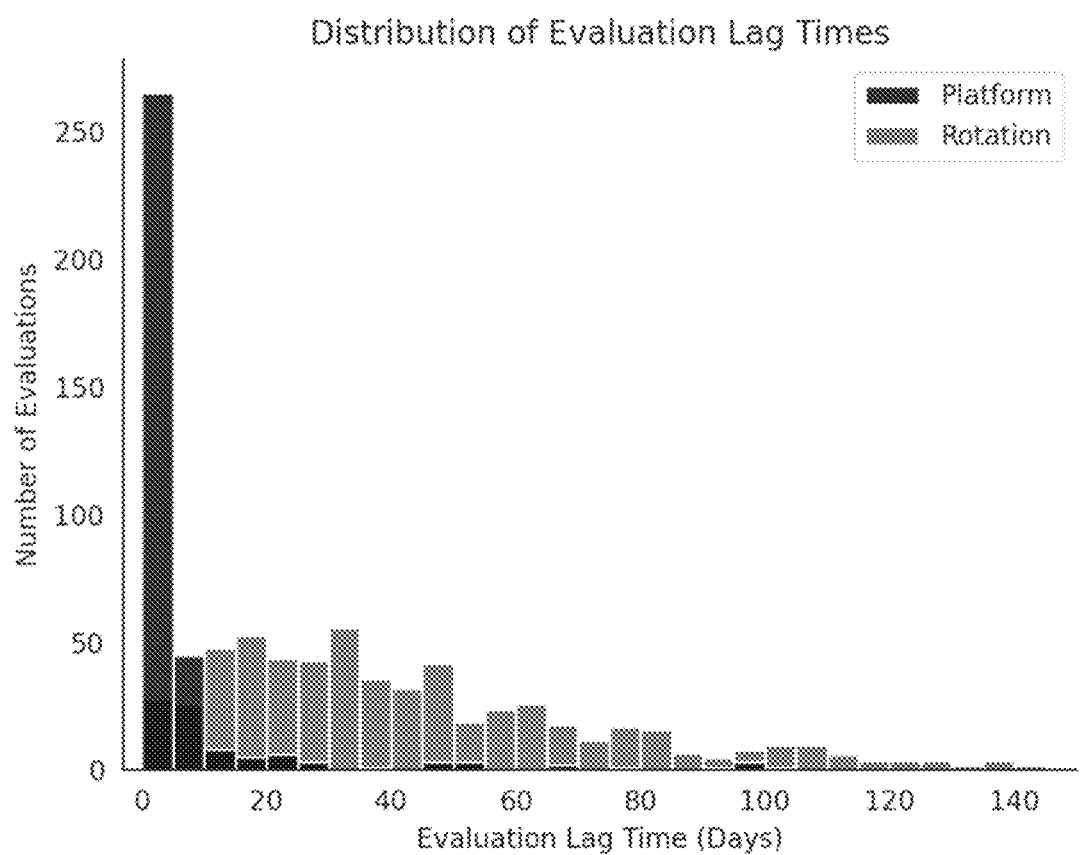
FIG. 14 shows a plot of number of evaluations versus evaluation lag time (in days) and the distribution of lag time for the methods and platform of the present invention for a given surgical rotation.

Results 358 platform evaluations were completed by 23 attendings for 43 residents for March through October 2017. 610 end-of-rotation evaluations by 15 attendings for 45 residents were used for comparison (September 2015 through June 2017). 41.3% of platform evaluations were completed within 24 hours of the operation (16.5% in 6 h, 33.3% in 12 h, 62.2% in 48 h) (FIG. 14).

In the first six weeks (March 1 through April 12) 4.5±3.7 evaluations were completed per week compared to 18.8±5.8 in the last six weeks (September 18 through October 31). Evaluation lag times improved with use of the platform, both for median lag of 35 days earlier (1±1.5 days platform, 36±28.2 days traditional, p<0.0001) and a mean lag of 41 days earlier (3.0±4.7 days platform, 44.0±32.6 days traditional, p<0.0001) (FIG. 14).

We defined the timeliness of evaluations to be the percent of evaluations submitted by a given lag time. The attendings submitted almost all of the evaluations within 5 days for the platform evaluations, and within 140 days for the end-of-rotation evaluations (FIG. 15.

From the timeliness, we used time thresholds to define evaluation compliance. The compliance was significantly higher for the platform evaluations (79%±2%) than for the end-of-rotation evaluations (16%±1%) (p-value <0.00001, FIG. 16). The attendings filled out the platform evaluations quickly, with 49% within one minute and 75% within two minutes (FIG. 17). Attendings typically submitted evaluations throughout the day, 81% during main operating hours 07:00 h to 18:00 h and 19% during evening hours. 24% of evaluations were completed within 3 hours after automated daily email reminders were sent at 17:00 h.

Conclusions

Our comprehensive platform facilitated faculty compliance with evaluation requirements and timeliness of availability of performance information (often in real-time or near real-time) for both residents and residency leadership. The platform aimed to improve the process of evaluation and the evaluator experience by three strategies: 1) limiting manual data entry by pre-populating relevant data, 2) focusing on ease-of-use to streamline workflow, and 3) increasing value for evaluators by combining evaluation with case logging connected to achievement of Maintenance of Certification (MOC) requirements. Platform features related to the latter strategy eliminated the need to enter case details or to select the assigned resident, and made any editing of these details simple. The platform's ease-of-use made initial instruction simple with the primary focus on login procedure and familiarity with the evaluation instrument. Based on our results, most importantly the rapid completion of the evaluations, the goal of facilitating the resident operative evaluation process was met. This process rapidity increased the likelihood that feedback was either delivered face-to-face, or reached the resident soon enough to be meaningful. This effect was not measured but is nonetheless one of the major goals: To enable positive feedback loops in user interaction in order to promote compliance and engagement. Although we did not survey user subjective reactions, we propose that the platform actually reduced the work burden that would have been experienced if the evaluation and logging tasks had been performed outside the common platform, and that this likely facilitated the prompt completion of evaluations we observed. The provision of automatic populating of data fields with case information was a major factor in reducing keyboard, mouse, and screen interactions to a minimum.

Longitudinally performed evaluations can serve as a means to demonstrate resident learning and improvement during a specific rotation, or over longer periods of time. Although rotation evaluations are a substantially different construct in that these require consensus input from multiple faculty members and are not deemed "complete" until all input is received, they represent a task at the opposite end of the effort spectrum. Not surprisingly, we observed rates of completion of rotation evaluation that reflected gradual accumulation of information which, while useful, delayed availability in many cases to a degree that almost certainly diminished their usefulness as feedback tools. There is an opportunity to look at this process differently based on the benefits of optimizing workflow. The platform can be used to automate the merging of evaluation information across faculty members, in order to create self-assembling consensus evaluations. The platform can gather case-based evaluations for a resident, and then present a summary of these evaluations to the evaluating faculty member as a reminder of the resident's performance over the rotation period. The faculty member can submit a streamlined end-of-rotation evaluation, including overall performance scores, feedback, and suggestions. As each evaluating faculty member completes the evaluations, the platform can assemble them into an inferred consensus evaluation, showing the distribution of the resident's performance scores as well as aggregated comments from the teaching faculty.

A positive feedback loop is further enabled by the analytics dashboard. The platform's real-time analytics dashboard presents tangible evaluation results so that they are easy to find and are understandable. Residents can see evaluative scores improve with practice and experience, incenting further practice and experience. Faculty members can see how many evaluations they have completed compared to their peers, incenting greater compliance with program evaluation needs. The dashboard provides the program director with an aggregated view of the evaluation results, in order to monitor resident progress and identify situations where directed action might be required to help with skills development.

Other commonly-used surgical resident evaluation tools exist, such as System for Improving and Measuring Procedural Learning (SIMPL) (19), and have similar goals of making evaluation process more convenient and accessible. One of the chief differences between these approaches and our platform is that our platform is agnostic to evaluation type. As we move forward with platform-based evaluation applications, it will be possible to capitalize on this to integrate evaluation instruments with a variety of intended purposes, including comparison studies or use of "best-practice" tools as they are developed. We have integrated Operative Performance Rating System (OPRS) evaluations required by the American Board of Surgery as well as resident self-efficacy evaluations (20), which are being compared to attendings' assessments. Another difference is that, instead of relying on residents to request being evaluated, the platform integrates with the hospital schedule and case assignments, and therefore it automatically detects when an evaluation event should occur. The schedule integration enables the platform to protect attendings and residents from forgetting to evaluate by targeted, case-specific daily reminder emails. The automated end-of-day and subsequent daily reminder emails might be a help to time-taxed attendings who wish to complete evaluations and log their cases, but we also found that these were not necessary for the majority of cases.

With the integrated schedule, the platform shows evaluation status as buttons embedded into the surgical schedule. This convenience saves the evaluator from having to track evaluations manually, in order to know whether any residents still require evaluations for the week's cases.

The schedule integration also enables convenient look-up of case details, which can help to jog the memory of the residents' actions and facilitate rapid completion of the performance scoring. Unlike with stand-alone evaluation tools, the evaluator does not need to describe the case procedure details or select the intended resident, since these data are pulled from the schedule.

Perhaps the platform's most unique differentiator is its integration with case logging systems. Since the ACGME makes case logging mandatory for residents, and the American Board of Surgery requires an accounting of cases for MOC, the platform's ability sync with the residents' ACGME case log and the ACS-SSR makes reduced interface burdens a benefit that can be experienced on a nearly daily basis. We have now learned that, when the process is sufficiently convenient, busy attending surgeons will integrate it into their daily post-operative workflow. Due to the streamlined evaluation process and extra incentive of case logging, throughout the study we saw increasing participation, whereas only 35% of attendings and 36% of residents reported using SIMPL after 20% of cases (21). We are also expanding the platform to other surgical subspecialties by integrating with their case logging systems, including the Mastery of Breast Surgery case log (22). By synthesizing the information within the platform, our long-term goal is to measure the impact of the evaluations on resident operative performance and to measure learning rates for individual residents and individual operations.

Referring to the figures, FIG. 1 shows how the platform system architecture connected disparate data systems, such as the hospital schedule and case logging systems, and surgery residents and teaching faculty. Although not shows, the platform's Case History page would show a surgeon's queue of recent cases, along with relevant actions for case logging and evaluating. The Case History page can include colored action buttons to indicate those actions that still needs to be performed. A "queued" log state means that the case has been logged into Firefly and is queued for automatic logging into an external case log, such as the ACS SSR or Mastery of Breast Surgery (MBS).

FIG. 14 shows a histogram of the distribution of evaluation lag times for platform evaluations and end-of-rotation evaluations.

Figure 15:
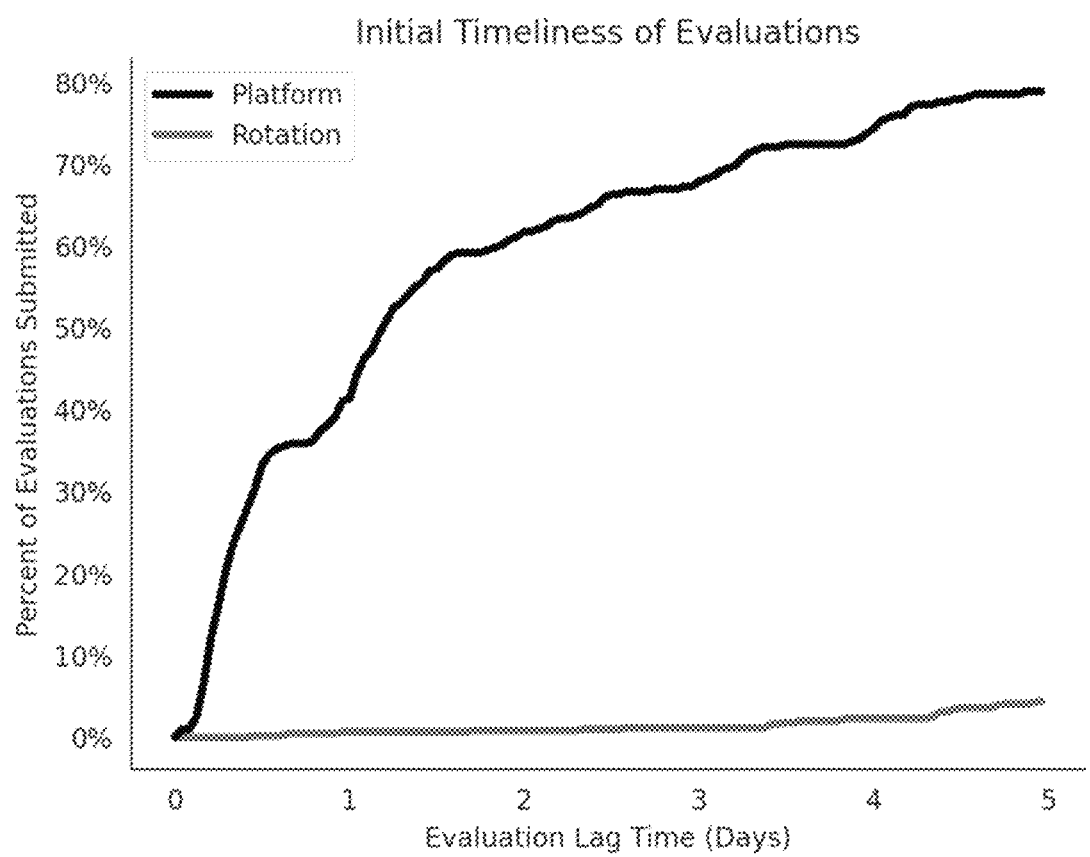
FIG. 15 shows a plot of percent evaluations submitted versus evaluation lag time (in days) for the methods and platform of the present invention for a given surgical rotation.

FIG. 15 is a timeliness plot showing the percent of evaluations submitted by a given lag time. Almost all the end-of-rotation evaluations were submitted within three months (A), whereas almost all the platform evaluations were submitted within 5 days (B).

Figure 16:
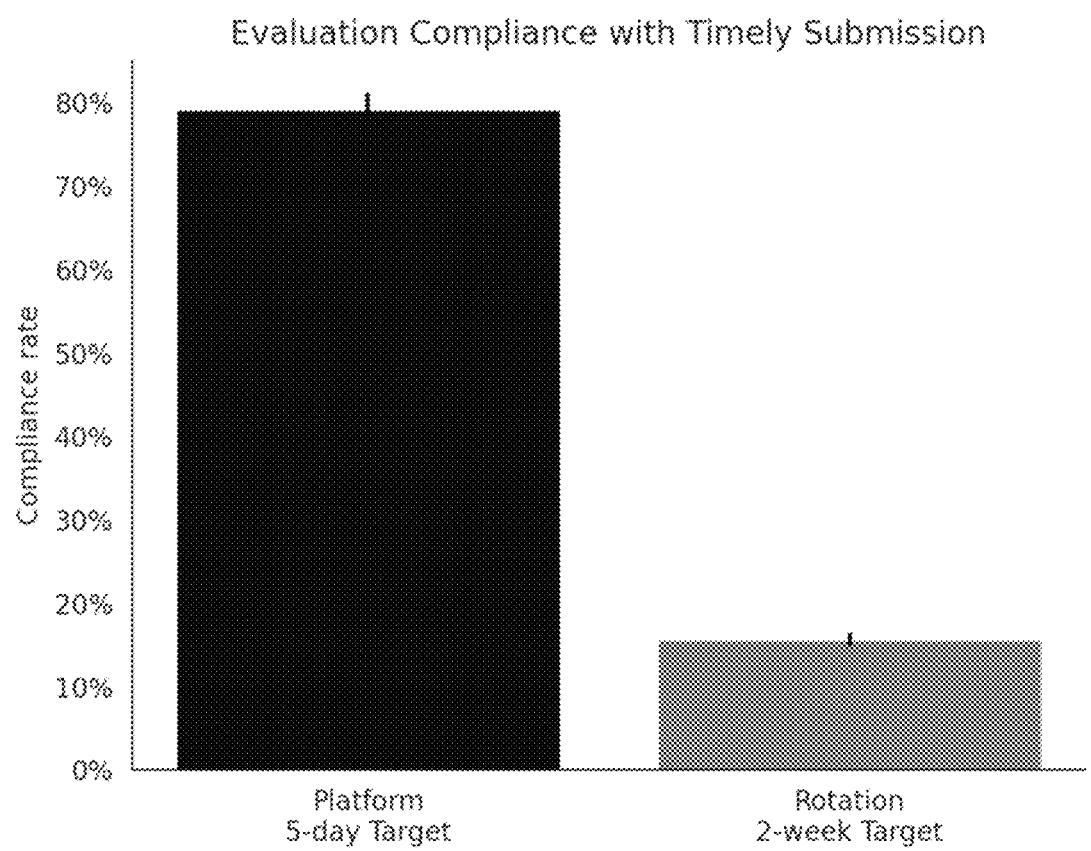
FIG. 16 shows a bar graph plot of compliance rate for evaluation compliance with timely submission for the methods and platform of the present invention for a given surgical rotation.
Figure 17:
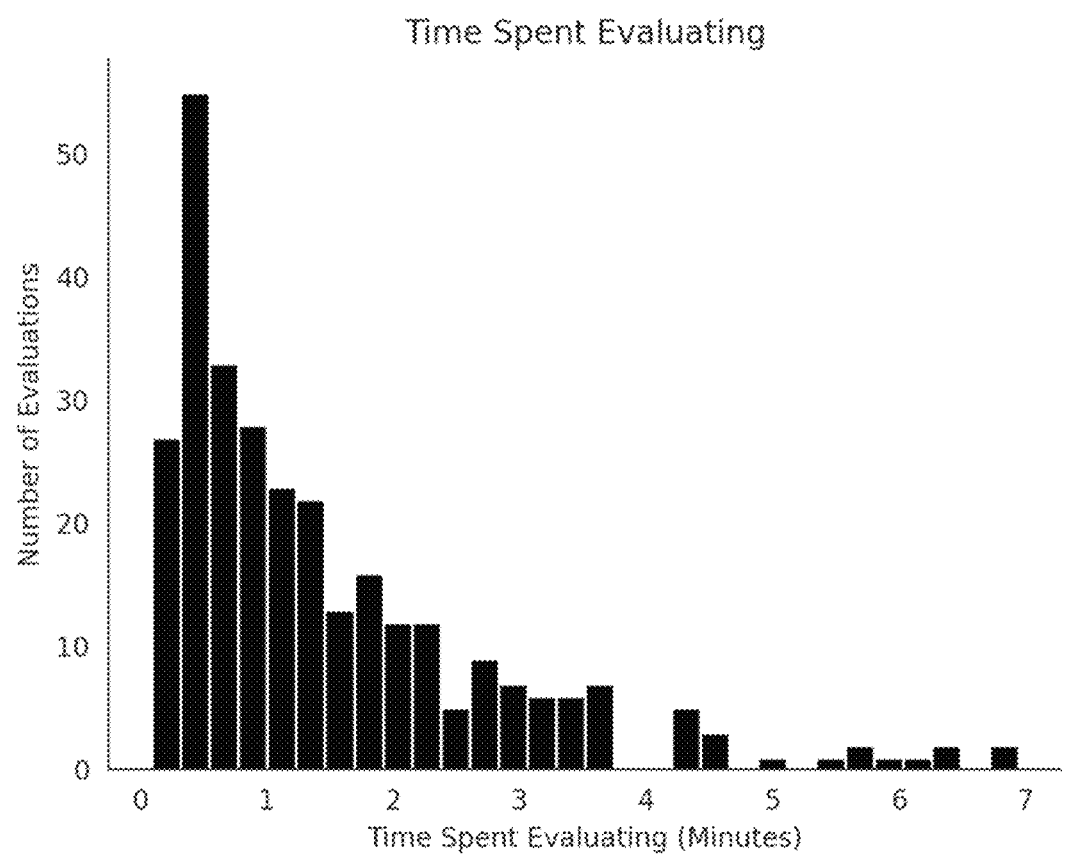
FIG. 17 shows a plot of the number of evaluations versus time (in minutes) spent evaluating a surgical resident.

FIG. 16 is a bar graph showing that evaluation compliance rates were significantly higher for the Platform evaluations (79%) than for the End-of-Rotation evaluations (16%) (p-value <0.00001).

FIG. 17 is a histogram of time spent evaluating that shows that the majority of Platform evaluations were done in less than two minutes. Also, the histogram of evaluation submission times confirmed that Platform evaluations were submitted throughout the day.

REFERENCES FOR EXAMPLE 1 ABOVE

1. Williams, R. G, Kim, M. J., and Dunnington, G. L, 2016. Practice guidelines for operative performance assessments. *Annals of surgery,* 264(6), pp. 934-948.
2. Karim, A. S., Sternbach, J. M., Bender, E. M., Zwischenberger, J. B. and Meyerson, S. L., 2017. Quality of Operative Performance Feedback Given to Thoracic Surgery Residents Using an App-Based System. *Journal of surgical education,* 74(6), pp. e81-e87.
3. Roberts, N. K., Williams, R. G., Kim, M. J. and Dunnington, G. L., 2009. The briefing, intraoperative teaching, debriefing model for teaching in the operating room. *Journal of the American College of Surgeons,* 208(2), pp. 299-303.
4. Dougherty, P., Kasten, S. J., Reynolds, R. K., Prince, M. E. and Lypson, M. L., 2013. Intraoperative assessment of residents. *Journal of Graduate Medical Education,* 5(2), pp. 333-334.
5. Roberts, N. K, Brenner, M. J, Williams, R. G, Kim, M. J. and Dunnington, G. L., 2012. Capturing the teachable moment: a grounded theory study of verbal teaching interactions in the operating room. *Surgery,* 151(5), pp. 643-650.
6. Raj M Ratwani, Rollin J Fairbanks, A Zachary Hettinger, Natalie C Benda; Electronic health record usability: analysis of the user-centered design processes of eleven electronic health record vendors, *Journal of the American Medical Informatics Association,* Volume 22, Issue 6, 1 Nov. 2015, Pages 1179-1182, https://doi.org/10.1093/jamia/ocv050.
7. Sittig, D. F. and Singh, H., 2011. Defining health information technology-related errors: New developments since To Err Is Human. *Archives of internal medicine,* 171(14), pp. 1281-1284.
8. Johnson C M, Nahm M, Shaw R J, et al. Can Prospective Usability Evaluation Predict Data Errors? *AMIA Annual Symposium Proceedings.* 2010; 2010:346-350.
9. Shanafelt, T. D., Dyrbye, L. N., Sinsky, C., Hasan, O., Satele, D., Sloan, J. and West, C. P., 2016, July. Relationship between clerical burden and characteristics of the electronic environment with physician burnout and professional satisfaction. In *Mayo Clinic Proceedings* (Vol. 91, No. 7, pp. 836-848). Elsevier.
10. Bohnen, J. D., George, B. C., Williams, R. G., Schuller, M. C., DaRosa, D. A., Torbeck, L., Mullen, J. T., Meyerson, S. L., Auyang, E. D., Chipman, J. G. and Choi, J. N., 2016. The feasibility of real-time intraoperative performance assessment with SIMPL (system for improving and measuring procedural learning): early experience from a multi-institutional trial. *Journal of surgical education,* 73(6), pp. e118-e130.
11. Wagner, J. P., Chen, D. C., Donahue, T. R., Quach, C., Hines, O. J., Hiatt, J. R. and Tillou, A., 2014. Assessment of resident operative performance using a real-time mobile Web system: preparing for the milestone age. *Journal of surgical education,* 71(6), pp. e41-e46.
12. Sehli, D. N., Esene, I. N. and Baeesa, S. S., 2016. A proposed Resident's operative case tracking and evaluation system. *World neurosurgery,* 87, pp. 548-556.
13. Hartranft, T. H., Yandle, K., Graham, T., Holden, C. and Chambers, L. W., 2017. Evaluating Surgical Residents Quickly and Easily Against the Milestones Using Electronic Formative Feedback. *Journal of surgical education,* 74(2), pp. 237-242.
14. American Medical Association: CPT—Current Procedural Terminology. www.ama-assn.org/ama/pub/physician-resources/solutions-managing-your-practice/coding-billing-insurance/cpt.pagewww.ama-assn.org/ama/pub/physician- resources/solutions-managing-your-practice/coding-billing-insurance/cpt.page
15. Gofton, W. T., Dudek, N. L., Wood, T. J., Balaa, F. and Hamstra, S. J., 2012. The Ottawa surgical competency operating room evaluation (O-SCORE): a tool to assess surgical competence. Academic Medicine, 87(10), pp. 1401-1407.
16. New Innovations. https://www.new-innov.com/. Accessed Apr. 1, 2018.
17. Corder, G. W. & Foreman, D. I. (2014). Nonparametric Statistics: A Step-by-Step Approach, Wiley. ISBN 978-1118840313.
18. Coombs, W. T., Algina, J. and Oltman, D. O., 1996. Univariate and multivariate omnibus hypothesis tests selected to control Type I error rates when population variances are not necessarily equal. *Review of Educational Research,* 66(2), pp. 137-179.
19. George, B. C., Teitelbaum, E. N., Meyerson, S. L., Schuller, M. C., DaRosa, D. A., Petrusa, E. R., Petito, L. C. and Fryer, J. P., 2014. Reliability, validity, and feasibility of the Zwisch scale for the assessment of intraoperative performance. *Journal of surgical education,* 71(6), pp. e90-e96.
20. de Blacam, C., O'Keeffe, D. A., Nugent, E., Doherty, E. and Traynor, O., 2012. Are residents accurate in their assessments of their own surgical skills?. *The American Journal of Surgery,* 204(5), pp. 724-731.
21. Eaton, M., Scully, R., Yang, A., Schuller, M., Smink, D., Williams, R., Bohnen, J., George, B., Meyerson, S., Karmur, A., Fryer, J., 2018, Value and barriers to use of a SIMPL tool for resident feedback, paper presented to Surgical Education Week, Association of Program Directors in Surgery, Austin, Tex., May 2018
22. Mastery of Breast Surgery, the American Society of Breast Surgeons https://masterybreastsurgeons.org Example 2

Education Management Platform Enables Delivery and Comparison of Multiple Evaluation Types The following are summary points from this Example 2:

The education management platform demonstrated a convenient method to deliver multiple operative evaluations intelligently matched to the appropriate operations. The platform delivered multiple appropriate evaluations together for the same cases provides an opportunity to study resident performance across operative evaluations. The platform-based evaluations can be completed in under a minute with an additional 1-2 minutes if comments are added The purpose of the work described in this example is for making multiple surgical evaluation instruments available when needed for appropriate clinical situations, including specific case types, presents some challenges that might impede convenient usage. We evaluated the impact of simultaneously delivering two evaluation instruments via a secure web-based education platform to test how easily these could be completed by faculty surgeon evaluators when rating resident operative performance, and how effectively the results of evaluation could be analyzed and compared, taking advantage of a highly integrated management of the evaluative information.

Methods:

We built a HIPAA-compliant web-based platform to track resident operative assignments and to link embedded evaluation instruments to procedure type. The platform matched appropriate evaluations to surgeons' scheduled procedures, and delivered multiple evaluations, including Ottawa O-Score autonomy evaluations and Operative Performance Rating System (OPRS) evaluations. Prompts to complete evaluations were made through a system of automatic electronic notifications. We compared the time spent in the platform to achieve evaluation completion. For those cases for which faculty completed both O-Score and OPRS evaluations, correlation was analyzed by Spearman rank test. Evaluation data were compared between PGY levels level using repeated measures ANOVA.

Evaluation of performance is an essential responsibility of the teaching faculty members of any surgical residency. Although the Accreditation Council for Graduate Medical Education (ACGME) explicitly defines this responsibility in section V of the Common Program Requirements, specific evaluation instrument types, specific methods to achieve timely completion, control of evaluation quality, and effective use as tools to facilitate positive development are areas where training programs have enormous latitude to utilize innovative methods. The use of evaluation as a feedback tool is vitally important in surgical training, and although published evidence of obstacles to achievement of effective feedback are scant, this issue is nonetheless frequently cited in the context of time pressures and conflicting responsibilities experienced by faculty members. There is agreement that absence of effective feedback is an impediment to high quality medical training (1), and that frequent evaluations are required for effective resident assessment (2-5).

The most useful system of evaluation is one that evaluators will be most apt to use (6), provided it offers an opportunity to deliver an assessment opportunity that is appropriate to the person being evaluated and sufficient detail so as to create a meaningful understanding of what has been observed without being excessively long and complex. Some evaluation types are useful in very specific settings. For example, an assessment of operative skills would be of no use in evaluating a resident's history-taking skills in the ambulatory office. An inventory or menu of evaluation types is needed to provide rich information on the ACGME competencies, and this can be comprised of any of a large number of established evaluation instruments. Accessing this when they are needed might be cumbersome as best, and impossible in the worst circumstances. Increasing faculty member efforts to complete evaluations would require a simple front-end experience to access a desired evaluation type, and rapid but invisible back-end processing of the entered information to make it available to both the learner and to the education leadership infrastructure. Faculty participation in resident evaluations will be greatly enhanced unnecessary workload is kept to a minimum. We sought to accomplish this with creating an automated evaluation selection and delivery system that would identify appropriate evaluations for residents in teaching cases and deliver them automatically to the corresponding teaching faculty.

Material and Methods

We built a secure, HIPAA-compliant, web-based platform for resident education management (7). The platform facilitated and tracked several aspects of resident education and performance, including case assignments, case logging, case outcomes, reading of targeted educational materials, and operative performance evaluations. The platform synced with operating room (OR) schedules and resident service rotation schedules to enable live case assignments and automatic matching of case details with evaluations. Based on the case procedure details and case staff, the platform identified relevant evaluations from a bank of available evaluations, including the Ottawa O-Score instrument rating of operative autonomy (8), Operative Performance Rating Systems (OPRS) evaluations (9), Entrustable Professional Activities (EPA) evaluations, Trauma non-operative evaluations, and resident self-evaluations. All evaluations were automatically paired with appropriate teaching cases and layered onto the operative schedule, where faculty and residents could easily find them and work them into their daily workflow. Faculty could choose whether to fill out one or more appropriate evaluations for each teaching case. For any teaching cases that still needed evaluations at the end of each day, the platform automatically sent brief reminder emails to the attendings to complete the evaluations, and upon completion it immediately pushed the evaluation results to the residents. Evaluation results were streamed into resident performance dashboards for residents, faculty, and program directors. The dashboards tracked resident learning with case experience, operative performance, and progress towards Accreditation Council for Graduate Medical Education (ACGME) requirements. The platform has been deployed multi-institutionally and across several departments.

For an initial test of the evaluation data quality, we measured the ability of the operative scores to stratify the residents by their program year (PGY) levels. Then, our principal measure of the usability of the platform's evaluation system was the time faculty spent to complete the evaluations. Each evaluation was structured as short set of Likert-scale questions, followed by optional comments. We split the evaluation responses into two sets, those with and those without comments, and on each set we measured the distribution of completion time using a Student's T-test with unequal variance, and linear models.

Delivering multiple appropriate evaluations together for the same cases afforded a unique opportunity to study resident performance across operative evaluations. We identified cases where faculty completed both O-Score and OPRS evaluations on the same resident. For these matching evaluations, we measured the Spearman rank-order correlation of the resident overall operative performance. We also investigated whether faculty completed both evaluations together in one sitting or at separate times. We measured the evaluation lag as the number of days between the teaching case and then submission of the corresponding evaluation. Finally, we explored correlations between pairs of questions across the evaluations.

Figure 4:
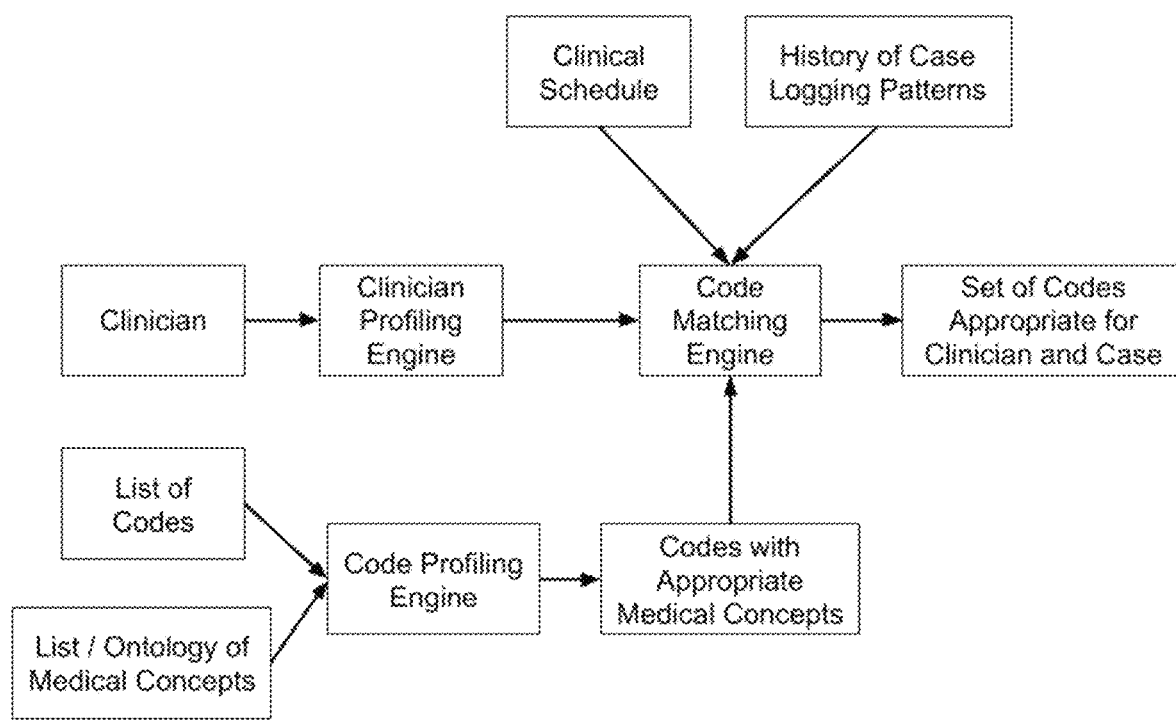
FIG. 4 is a diagram showing the data flow and processing for the code matching engine to identify and rank order smart suggestions and smart search for appropriate medical codes for medical activities.

Results 1,230 O-Score evaluations, 106 OPRS evaluations, and 14 EPA evaluations were completed by 33 attendings for 67 residents from March 2017 to February 2019. Evaluations were completed quickly, with the completion time depending mostly on the level of detail that the attending chose to include in the optional comments. For evaluations without comments, the median completion times were 36±18 seconds for O-Score evaluations and 53±51 seconds for OPRS evaluations. For evaluations with comments, the times increased to 1.79±1.12 minutes for O-Score and 1.87±1.09 minutes for OPRS (t-test with unequal variance, $p<0.00001$) (FIG. 2-3). The overall evaluation completion time varied approximately linearly with comment length ($r=0.85$, $p<0.00001$ for O-Score, and $r=0.54$, $p=0.001$ for OPRS) (FIG. 2-4).

Figure 18:
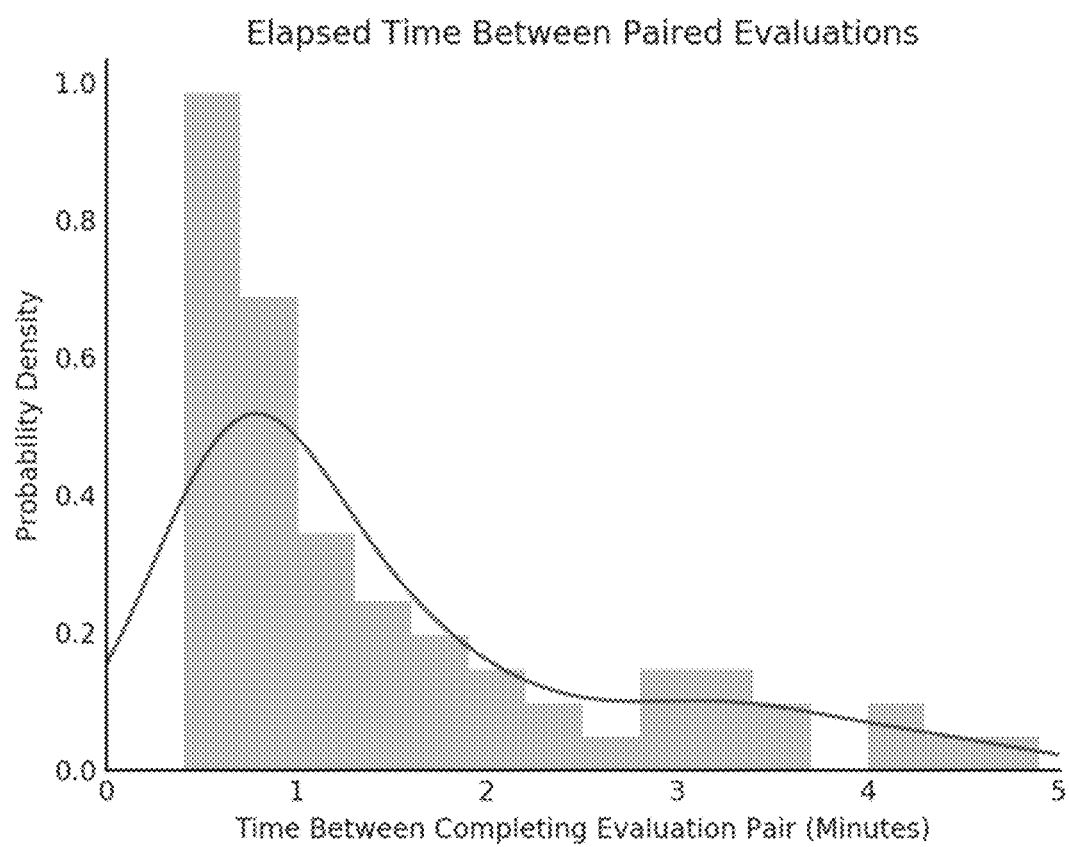
FIG. 18 shows a plot illustrating the elapsed time (in minutes) between paired evaluations, i.e. where two or more evaluations are provided to a given surgical resident by the attending surgeon. The "paired" evaluations can be for either the same or different procedures.

There were 74 teaching cases for which faculty completed both the O-Score and OPRS evaluation for the same resident, allowing for direct analysis of the timing and scoring across the paired evaluations. Faculty almost always completed both evaluations in one session, within a few days of the case (robust linear regression, $r=0.97$, $p<0.0001$) (FIG. 2-5) and within 1 minute±38 seconds of each other (FIG. 18).

Figure 19:
FIG. 19 shows a plot of resident performance across evaluations Operative Performance Rating System (OPRS) overall score versus O-score overall score. [To move the next two sentences to the detail description or Examples section.] The Operative Performance Rating System (OPRS) is a set of procedure-specific rating instruments and recommended methods for observing and judging single performances of nine operative procedures frequently performed by general surgeons(1) and by general surgery residents(2) in training. The O-score is the Ottawa Surgical Competency Operating Room Evaluation (O-SCORE), is a 9-item surgical evaluation tool designed to assess technical competence in surgical trainees using behavioral anchors.

The paired evaluations showed high correlation for resident overall operative performance (Spearman's rho=0.84, $p<0.00001$) (FIG. 19). We measured the correlation across all pairs of questions across evaluations. The pairwise correlations were consistently high (rho>0.7) with the except of knot tying, which showed very little correlation across the other skills.

Conclusions

The platform enabled flexibility in the evaluation process of resident operative performance. By integrating data from the department OR schedules, faculty staff profiles, resident profiles, and multiple types of evaluations, the platform automatically identified teaching cases and matched them with appropriate evaluations. By removing the friction from the evaluation selection and delivery process, it was much easier for time-pressed faculty to participate and complete their evaluations, even multiple evaluations per case. The platform improved the evaluation process for three relevant parties: 1) Faculty see appropriate evaluations in their personal operative schedules and get automated reminder emails, 2) Residents get much more timely feedback on their performance, and they don't have to do any set-up work to create the evaluations or send them to their attendings, and 3) Program directors experience much higher compliance rates from their teaching faculty and see their residents' performance trends in a real-time dashboard. One goal of the evaluation delivery system was to enable a virtuous feedback-and-learning cycle, where faculty would participate more, feeling that their evaluating time was valuable, as their feedback was delivered to the residents in real time soon after each case. And the residents would learn earlier how to improve their performance, and therefore demonstrate accelerated improvement throughout their service rotation with the faculty.

The proactive delivery and sub-minute completion times of the evaluations help explain their sustained use. The Likert-scale evaluations were short and quick enough for the faculty to fold into their daily workflow without much burden, and the evaluation comments allowed for additional feedback and guidance to the residents as needed. The paired evaluations demonstrated generally high correlations across their questions, indicating a well-balanced skills progression as residents gained operative experience. However, the notable outlier was knot tying, which showed no correlation to the other skills. Perhaps knot tying is a mechanical skill that is taught early in surgery residency and can be practiced in isolation, before the resident has the experience or background knowledge needed for higher-level skills, such as planning and decision-making in the OR, and general efficiency with time and motion during procedural steps. By comparing questions from several evaluation sources, it becomes possible to find an optimal set of predictive questions that minimize faculty burden and therefore maximize faculty participation, and maximize actionable utility to the residents. Multi-evaluation data collected in a large scale can possibly reorient and accelerate the evaluation design process. Rather than carrying out a prolonged study to validate a fixed evaluation, a platform that continuously tracks faculty participation and resident performance improvement could enable a "rolling" strategy for prioritizing and selecting informative and actionable questions from several sources and packaging them into optimal, short evaluations delivered to the right faculty at the right time in their residents' educational journeys.

As a next step for the educational platform, these case-based evaluations can be combined and summarized into self-assembling consensus evaluations. The platform can present a coherent summary of all the recent evaluations to the evaluating faculty member, to facilitate the completion of end-of-rotation evaluations. The performance data could also be aggregated and structured according the ACGME milestones for program-level reporting. Currently, we are also helping faculty build their own custom procedure-specific evaluations, targeted at important procedural steps in common case types.

Referring to the figures, FIG. 1 shows how the platform integrates data from the OR schedule and assigned case staff, along with a data bank of available evaluations, to find appropriate evaluation and match them to each teaching case.: The two evaluations stratified the residents across program year levels ($p<0.0001$). A larger average ORPS performance score for PGY 1 residents could have resulted from less complex cases appropriate for beginning surgery residents.: Faculty completed the evaluations quickly, especially when they opted not to include the optional comments ($p<0.00001$).: Most of the evaluation time was due to writing comments ($p<0.0001$).: Faculty almost always completed both evaluations together, within a few days of performing the case with the resident ($p<0.0001$).

FIG. 18 show a plot of the paired O-Score and OPRS evaluations, faculty completed evaluations in rapid sequence, within 1 minute±38 seconds. FIG. 19 shows the distribution for paired O-Score and OPRS evaluations showed high correlation (rho=0.84, $p<0.00001$) for resident overall operative performance. The size of the dots indicates the number of matching evaluations at each score level.: Comparing questions across multiple matched evaluations enables a detailed view of the response patterns. In this subset, most questions demonstrated moderate correlation, with the exception of knot tying. Perhaps because knot tying is an early-level mechanical skill, it did not correlate with broader skills that require more experience and background knowledge.

REFERENCES FOR EXAMPLE 2, ABOVE

1. Anderson P A. Giving feedback on clinical skills: are we starving our young? J Grad Med Educ. 2012; 4:154-8
2. Williams R G, Verhulst S, Colliver J A, Sanfey H, Chen X, Dunnington G L. A template for reliable assessment of resident operative performance: assessment intervals, numbers of cases and raters. Surgery. 2012 October; 152(4):517-24; discussion 524-7. doi: 10.1016/j.surg.2012.07.004. Epub 2012 Aug. 28.
3. Dougherty P, Kasten S J, Reynolds R K, Prince M E and Lypson, M L. Intraoperative assessment of residents. J Grad Med Educ. 2013 June; 5(2):333-4. doi: 10.4300/JGME-D-13-00074.1.
4. Williams R G, Swanson D B, Fryer J P, Meyerson S L, Bohnen J D, Dunnington G L, Scully R E, Schuller M C, George B C. How Many Observations are Needed to Assess a Surgical Trainee's State of Operative Competency? Ann Surg. 2019 February; 269(2):377-382. doi: 10.1097/SLA.0000000000002554.
5. Fryer J P, Teitelbaum E N, George B C, Schuller M C, Meyerson S L, Theodorou C M, Kang J, Yang A, Zhao L, DaRosa D A. Effect of Ongoing Assessment of Resident Operative Autonomy on the Operating Room Environment. J Surg Educ. 2018 March-April; 75(2):333-343. doi: 10.1016/j.jsurg.2016.11.018. Epub 2017 Mar. 28.
6. Williams R G, Kim M J, Dunnington G L. Practice Guidelines for Operative Performance Assessments. Ann Surg. 2016 December; 264(6):934-948.
7. Thanawala R, Jesneck J, Seymour N E. "Novel Educational Information Management Platform Improves the Surgical Skill Evaluation Process of Surgical Residents." *Journal of surgical education* 75.6 (2018): e204-e211.

8. Gofton W T, Dudek N L, Wood T J, Balaa F, Hamstra S J. The Ottawa Surgical Competency Operating Room Evaluation (O-SCORE): a tool to assess surgical competence. Acad Med. 2012 October; 87(10):1401-7.

9. Larson J L, Williams R G, Ketchum J, Boehler M L, Dunnington G L. Feasibility, reliability and validity of an operative performance rating system for evaluating surgery residents. Surgery. 2005 October; 138(4):640-7; discussion 647-9.

Example 3

Inferring Resident Autonomy for Surgical Procedures with Learning Curves

The American Board of Surgery expects residents to be proficient, safe, and autonomous across 132 "Core" surgical procedures in order to graduate and become practicing surgeons. For surgical educators, it can be a daunting task to solicit and assimilate performance feedback across a program's residents, especially in a timely, comprehensive, and quantitative manner. We propose a Bayesian learning curve model that incorporates surgical case history along with Likert-scale and Zwisch-scale evaluation data to infer and quantify resident operative autonomy.

Methods

We built a HIPAA-compliant web-based platform to track resident operative assignments and to link embedded evaluation instruments to procedure type. The platform delivered multiple evaluation types, including Ottawa O-Score autonomy evaluations. Autonomy scores were gathered across teaching faculty and combined with the residents' history of case assignments. For this analysis we focused on cholecystectomy cases. The data were entered into a Bayesian logistic learning curve model, including estimates for the resident's learning lag (the number of cases needed until rapid learning), the maximum learning rate, and the autonomy limit (the maximum autonomy level we expect the resident to achieve after a large number of cases). The learning curve model included an ordinal response component, which inferred the resident's actual autonomy level from the faculty's ordinal Likert-scale ratings. It also inferred the faculty's implicit "hawk or dove" grader bias, while accounting for reported case complexity. The model was applied to each resident across the program, creating a learning baseline against which each individual resident can be compared to his or her peers.

Results 129 evaluations for cholecystectomy cases were completed by 12 attendings for 31 residents over about 20 months. The learning curves for the residents clustered into an early-learning group of senior residents and a later-learning group of junior residents.

Figure 9:
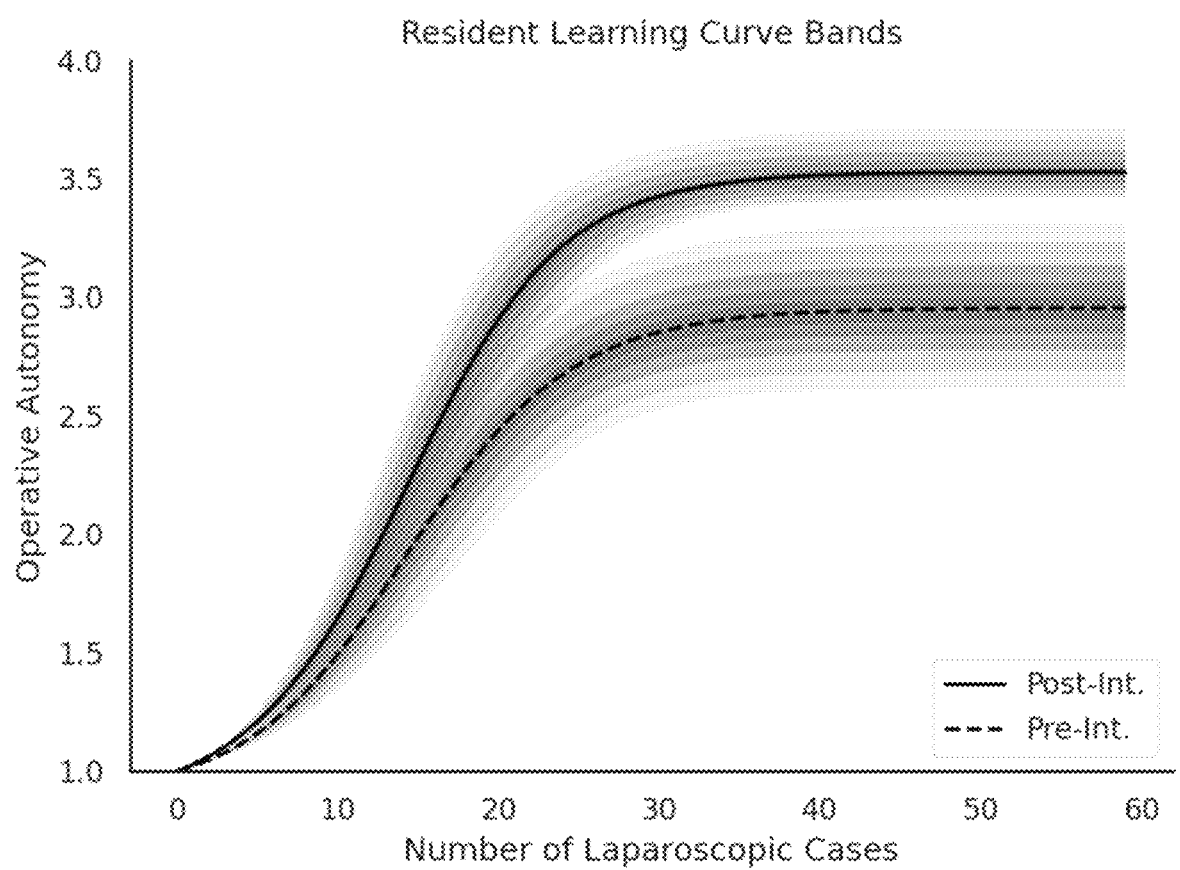
FIG. 9 is a plot showing the posterior samples of learning curves for the residents, before the teaching intervention and after the intervention of the present invention.
Figure 10:
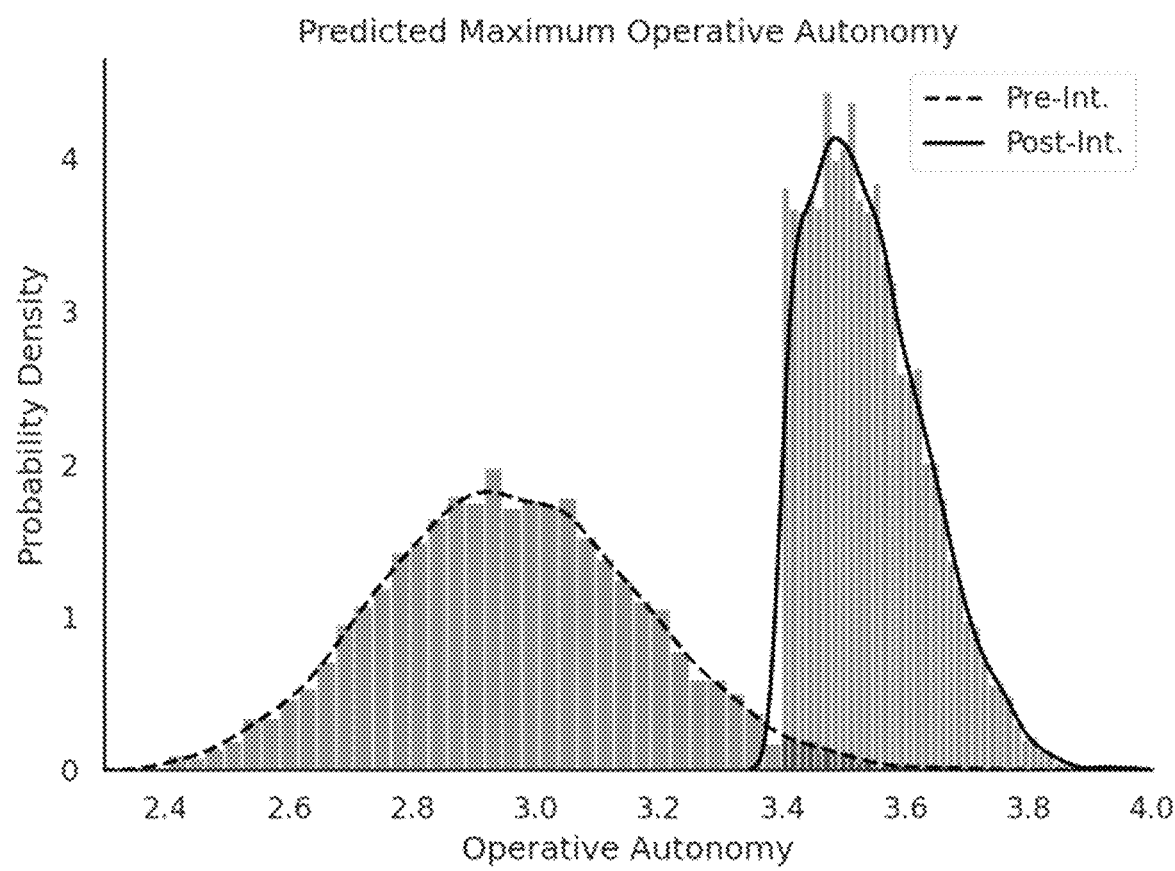
FIG. 10 shows a vertical slice cross-section of the bands at the far right of FIG. 9. This data relates to predictive distributions for maximum resident autonomy. These data show that the intervention worked and made those residents more independent in the operating room.

Referring to the figures, FIG. 9 shows learning curve distributions for pre vs post intervention. More specifically, this figure shows the learning curves for the residents, before the teaching intervention and after the intervention. By "intervention", is meant that they were given extra training, support, and practice exercises by their teaching faculty, in order to help bring their operative performance up to an acceptable level. Here the learning bands show the distribution of the learning curves. The width of the bands show the model confidence. The dense region in the middle is the most likely. As more evaluations are added, the model will have further data to work with and can iteratively produce more confident predictions, so the bands will likely converge. Also, it is seen that the teaching intervention was successful, because it shifted the residents' curve up, meaning that going forward they are likely to be more independent surgeons for laparoscopic cases.

FIG. 9 is a plot showing posterior samples of the learning curves for a group of residents as a function of cases performed.

Figure 13:
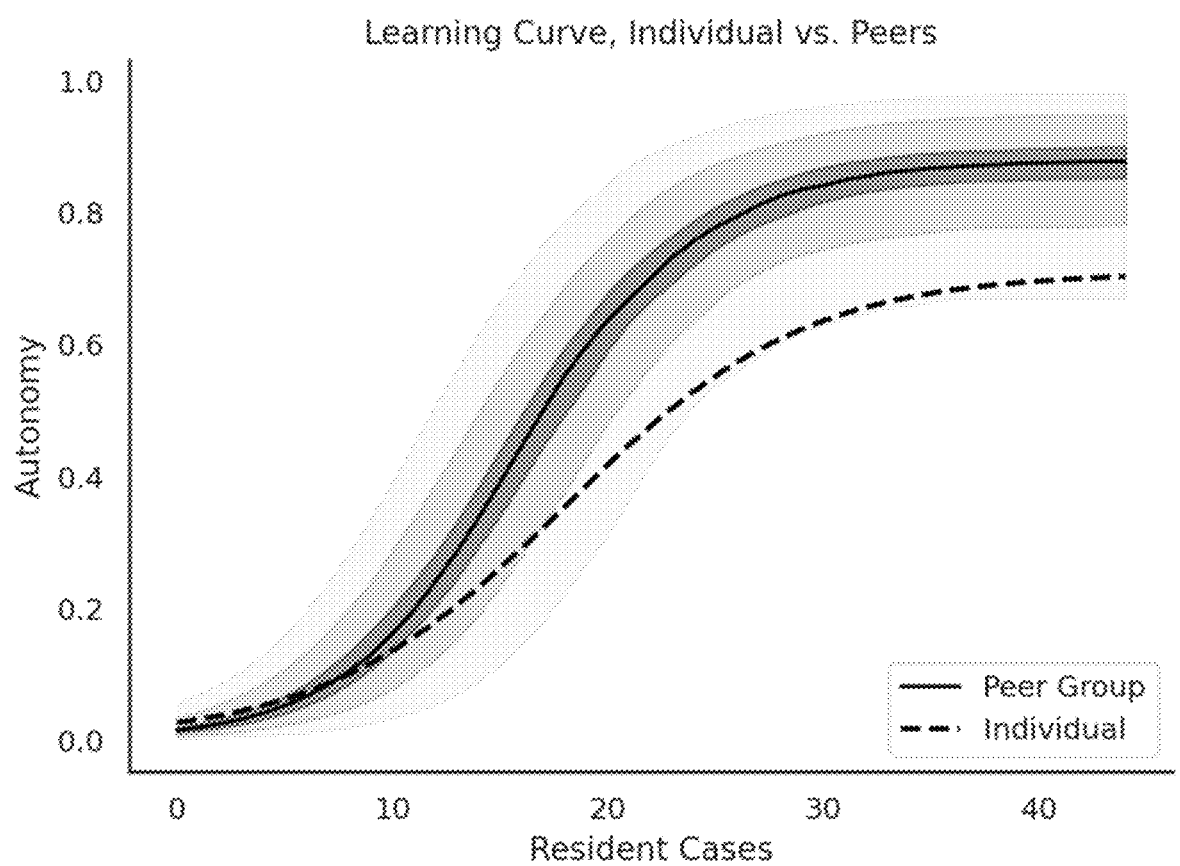
FIG. 13 is a plot showing the learning curves for a group of residents as a function of cases performed. The y-axis shows the level of autonomy rating, from lowest to highest: attending surgeon performed; steered; prompted; back-up, and auto as described further in Table 2. The y-axis shows the level of autonomy rating, from lowest to highest: attending surgeon performed; steered; prompted; back-up, and auto as described further in Table 2.

FIG. 13 shows a learning curve for an individual versus a composite of the learning curves for the peer group. The y-axis shows the level of autonomy rating, from lowest to highest: attending surgeon performed; steered; prompted; back-up, and auto as described further in Table 2.

Example 4

User Interface for Augmented Clinical Schedule:
This example row from a schedule shows a single case or patient encounter. With the case details are action buttons, for example for case logging, evaluating other case staff members, and editing the case details.

Matching Clinical Codes for Clinical Encounter Logging:
The code matching system aggregates clinical data, clinical schedules, and historical case logging data to match appropriate codes for each clinician and clinical encounter. See FIG. 4.

Matching Educational Content for Targeted Education:
The Targeted Education System aggregates medical educational content, clinical schedules, and clinician practice patterns to match appropriate, high-quality educational content to each clinical for upcoming clinical encounters. See FIG. 5.

Predicting Case Volume:
A) A medical learner's cumulative case volume over time. The volume is known from the start of his program until the present time, when statistical models are used to predict the case volume at a given future time, such as the learner's graduation date. The shaded area shows the credible band, and the center line shows the most likely value for the case volume. The horizontal dotted line shows the minimum number of cases required by the educational program, ACGME. See FIG. 25B.
B) The probability of achieving each number of cases at a given future time.

Example 5

Use of a Secure Web-Based Data Management Platform to Track Resident Operative Performance and Program Educational Quality Over Time Objective: In surgery residency programs, ACGME mandated performance assessment can include assessment in the operating room to demonstrate that necessary quality and autonomy goals are achieved by the conclusion of training. For the past three years, our institution has used The Ottawa Surgical Competency Operating Room Evaluation (O-SCORE) instrument to assess and track operative skills. Evaluation is accomplished in near real-time using a secure web-based platform for data management and analytics (Firefly). Simultaneous to access of the platform's case logging function, the O-SCORE instrument is delivered to faculty members for rapid completion, facilitating quality and timeliness of feedback. We sought to demonstrate the platform's utility in detecting operative performance changes over time in response to focused educational interventions based on stored case log and O-SCORE data.

Design: Resident performance for the most frequently performed laparoscopic procedures (cholecystectomy, appendectomy, inguinal hernia repair, ventral hernia repair) were examined over three successive academic years (2016-2019). During this time, 4 of 36 residents received program-assigned supplemental simulation training to improve laparoscopic skills. O-SCORE data for these residents were extracted from peer data, which were used for comparisons. Assigned training consisted of a range of videoscopic and virtual reality skills drills with performance objectives. O-SCORE response items were converted to integers and overall autonomy scores were compared before and after educational interventions (Student's t-tests). These scores were also compared to aggregate scores in the non-intervention group. Individual learning curves were used to characterize patterns of improvement over time.

Setting: Hospital Institutional Tertiary Care Center.

Participants: PGY2 through PGY4 general surgery residents (n=36).

Results: During the period of review, 3325 resident cases were identified meeting the case type criteria. As expected, overall autonomy increased with the number of cases performed. The four residents who had been assigned supplemental training (6-18 months) had pre-intervention score averages that were lower than that of the non-intervention group ($2.25 \pm 0.43$ vs $3.57 \pm 1.02$; $p<0.0001$). During the respective intervention periods, all four residents improved autonomy scores (increase to $3.40 \pm 0.61$; $p<0.0001$). Similar improvements were observed for tissue handling, instrument handling, bimanual dexterity, visuospatial skill, and operative efficiency component skills. Post-intervention scores were not significantly different compared to scores for the non-intervention group.

Conclusions: The Firefly platform proved to be very effective in tracking responses to supplemental training deemed important to close defined skills gaps in laparoscopic surgery. This could be seen both in individual and in aggregated data. We were gratified that at the conclusion of the supplemental training, O-SCORE results for the intervention group were not different than those seen in the non-intervention group.

Abbreviations: ACGME (Accreditation Council for Graduate Medical Education); O-SCORE (Ottawa Surgical Competency Operating Room Evaluation Score)

The skilled performance of surgery is extraordinarily demanding of practitioners at all levels of experience, and deficient surgeon skills are widely felt to negatively impact patient outcomes (1,2). Even with protections in place to limit duty hours, residency training in surgery continues to be arduous and lengthy with the overriding goal of preparing the trainee for safe, independent surgical practice. The process of training includes, by design, progressive withdrawal of direct supervision as experience, and commensurately, skills, knowledge, and confidence are gained. The Accreditation Council for Graduate Medical Education (ACGME) core program requirements for general surgery training (3) specify how this must occur in both general and specific terms. Educational tools that are expected to be used include access and exposure to core content, simulation, operative case experience under supervision (direct or indirect), and assessment methods that aim to both model and to make summative determinations about performance. Although all training programs seek to maximize residents' core competencies, the general means to accomplish this goal are not highly standardized, and in fact there is substantial "wiggle room" in designing curricula with substantial variations in nonclinical educational experiences.

Understanding each resident's areas of strength and weakness provides an opportunity to tailor training, including the use of simulation lab-based training, to the most applicable content needed to ensure efficient achievement of educational goals. The success of any such effort begins with the ability to identify the need for training and ends with demonstration that the desired performance has been attained. This requires effective assessment. Educational interventions that aim to address the training need(s) must also be available and utilized effectively in order to spur development. Effective assessment methods offer the opportunity to monitor performance on an individual basis and in groups of residents. With appropriate analytic capabilities, these performance data can provide a view of educational effectiveness at a programmatic level as well.

Having already shown that intelligent, technology-based operative assessment delivery along with incentivization of assessment completion (4) result in rapid availability of evaluations, we sought to determine if this established assessment model, when used with other evaluative data, could identify both the need for supplemental laparoscopic skills training and the collective effectiveness of our residency program's efforts to improve laparoscopic surgical performance based on the program's routine use these tools in the course of formative education.

Materials and Methods

Ottawa Surgical Competency Operating Room Evaluation (O-SCORE): The O-SCORE (5,6) is an instrument to assess operative skills of individual residents on a case-by-case basis. This tool was introduced to the Hospital Surgery Residency: The O-SCORE, as described by its University of Ottawa developers, is a 9-item evaluative tool designed to assess technical competence with 8 items related to preprocedural planning, case preparation, knowledge of procedure steps, technical performance, visuospatial skills, postprocedural plan, efficiency and flow, communication, and overall performance. These are rated using a scale intended to reflect the degree of autonomy or independence demonstrated to the evaluator (Table 2). An additional item, answered "yes" or "no", pertains to the residents' ability to do the case independently. In our implementation model, the form was expanded to 12 scaled items by specifying operative skills to include four separate items for evaluation of knot-tying, tissue handling, instrument handling, and ability to assist. Evaluations were delivered to faculty members using a secure web-based platform (Firefly Lab, Cambridge, Mass.) which matched the specific evaluation to the patient, proposed procedure, faculty member, and resident assigned to the case, using machine intelligence algorithms that also aided post-procedure case logging for both residents and faculty members (4). Evaluation and logging capabilities were optimized for use in web browser windows on both computers and hand-held devices. Firefly platform integrated analytics were used to obtain evaluative data over three successive academic years (2016-2019) for the four most frequently performed laparoscopic general surgery procedures: cholecystectomy, appendectomy, inguinal hernia repair, and ventral hernia repair. Integers on the autonomy scale ranged from 1 to 5, corresponding to attending "I had to do" continuing up to "I did not need to be there" representing maximum resident autonomy for all assessment items (Table 2). To make these descriptors more display-friendly on cell phone screens, they were shortened to terms such as "I did" and "Auto".

Training interventions: During the reviewed period, four of 36 residents, postgraduate year 2-4, were assigned individual learning plans consisting of supplemental simulation training with the aim of improving laparoscopic skills. The determination of need to receive this training was based on a combination of evaluative information sets that included O-SCORE results, end-of-rotation evaluations, and ad hoc commentary received by the Surgical Education Office. This determination was a subjective one made by the Surgical Education Committee and prompted preparation of individual learning plans that required at least weekly 1-hour sessions in the Hospital Simulation Center—Goldberg Surgical Skills Lab, beyond the normal weekly 1-hour simulation selectives assignments. Supplemental training consisted of a range of videoscopic and virtual reality skills drills with clear performance objectives and lab-based coaching for 30-52 weeks. During the period over which this training occurred, residents exercised their usual clinical responsibilities, including operative experiences.

O-SCORE data for these four residents were extracted from the peer data for other residents, which were used as a control dataset for comparison purposes. Numerical O-SCORE individual skills deemed relevant to their lab-based training as well as overall scores were analyzed. Numerical data are expressed as mean±standard error (or 95% confidence intervals for graphed data), and compared before and after supplemental educational interventions (paired Student's t-tests). These scores were also compared to aggregate scores in the non-intervention group (unpaired Student's t-tests). Grouped learning curves were modeled from longitudinal assessments and logged case numbers for individual residents. Bayesian methodology enables the calculation of the most likely learning curve for each resident group. By fitting the curve to the observed evaluation scores, it calculates the most likely values for the residents' learning rates and predicted maximum autonomy levels. We used a generalized logistic curve under a Bayesian statistical framework to compensate for the reality of fewer assessments than logged relevant cases. This model fitted curves to assessment data and inferred curve shape using Markov chain Monte Carlo sampling (7), and using the No-U-Turn Sampler (8) for computationally efficient sampling of the curve parameters for each group. The evaluation ordinal ratings were used to infer each resident's operative autonomy level, learning rate, and predicted maximum autonomy level. The model also inferred and accounted for case complexity and each teaching faculty member's "hawk vs dove" rater bias (9).

This retrospective analysis of resident performance was reviewed by the Hospital Institutional Review Board as a quality assurance activity and was deemed not to constitute human subjects research.

Results

During the period of review, 3325 logged resident cases and 369 O-SCORE assessments were identified as meeting the case type criteria. From these, 54 assessments were available for residents in the educational intervention group. As expected, Bayesian-modeled learning curves expressing interpolated performance showed that all residents improve as the number of cases performed increases. However, for residents determined to need supplemental training, the pre-intervention curve shows a clear pattern of performance lag relative to the non-intervention curve (FIG. 9), with suggestion of a blunted rate of improvement and a lower level of operative autonomy at the projected point of slowed rate of improvement (25-30 cases) compared to both the post- and non-intervention curves. Examining post-intervention performance, this performance deficit had improved substantially with the learning rate and the predicted maximum autonomy levels more closely resembling those of the non-intervention group (FIG. 9). Further, histogram analysis shows the posterior predictive value of the maximum autonomy level increased significantly from the pre-intervention to the post-intervention (p<0.0001, FIG. 10). However, these did not approach the much higher posterior predictive value of the nonintervention group which was based on a much larger number of observations.

Figure 11:
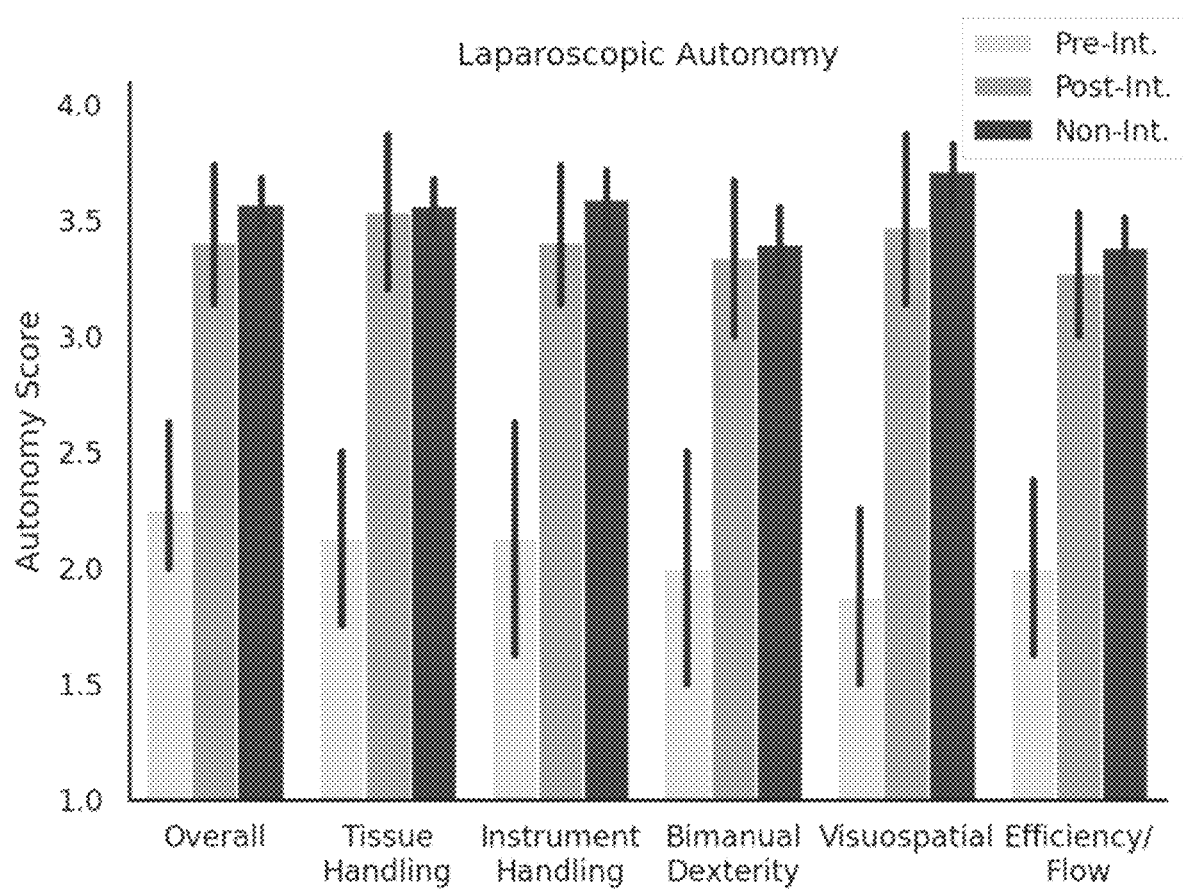
FIG. 11 shows a bar graph illustrating laparoscopic procedural autonomy for an intervention and non-intervention group of residents.

Examination of mean performance scores demonstrates a similar pattern of performance difference between pre- and post-intervention results for residents in the educational intervention group, and between this group and the non-intervention group (Table 3). During the six-month period prior to assignment of supplemental training, the four residents in the intervention group were noted to have average scores that were significantly lower than the non-intervention group averages ("overall" scores 2.25±0.43 vs 3.57±1.02 respectively; p<0.0001). Over the course of their respective intervention periods, all four residents improved O-SCORE results (increase in "overall" scores from 2.25±0.43 to 3.40±0.61; p<0.0001). In addition to overall autonomy, similarly significant improvements were observed for tissue handling, instrument handling, bimanual dexterity, and visuospatial component skills (FIG. 11). Although not necessarily the focus of lab-based training, "Efficiency and Flow" results showed similar improvements. During the post-intervention period for the educational intervention group, these component and overall scores were not significantly different from corresponding scores for the non-intervention group (Table 3).

Conclusions

In recent years, the surgical residency experience has changed in fundamental ways for trainees and faculty members, raising questions of whether the requisite skill levels for the independent practice of surgery can reliably be achieved by chief residents after completion of five years of clinical training. The cited factors that might impede this goal include limitations on hours worked (10), decreased exposure to a sufficiently large number and broad range of operations (11-13), and barriers to the offer of opportunities to exercise a high degree of independence during operative cases (14). Probably no less important, momentous changes in surgical methods and tools have undoubtedly added a layer of complexity to training that might impact opportunities for resident operative autonomy. Without strong mitigation steps, perhaps unsurprisingly, graduating residents might feel underprepared for independent practice or, as in one report, seem to underperform in the view of fellowship program directors when first confronted with common operative responsibilities (15,16). While it is difficult to draw broad conclusions from these observations without compelling data to suggest that patient outcomes are adversely affected, efforts have been made in the past few years to facilitate higher degrees of independent resident practice. This is especially important to achieve while the strong supervisory infrastructure associated with residency is available.

Among the ways improved resident preparation might be accomplished include increasing the number and range of opportunities to exercise independent practice safely (17). Active learning techniques improve knowledge acquisition and retention for surgical learners (18), and abundant experience shows that simulation methods can amplify surgical ability by providing practice of component skills and procedures outside of the operating room (19-21). It is widely accepted that use of simulation can increase trainee operative skills, and some limited data show that simulation training can improve selected patient outcomes (22). However, few studies have specifically examined the effects of simulation training on surgeon confidence or operative autonomy, and those that do are limited in sample size and scope (23,24). In addition, there is surprisingly little published experience with lab-based training as a tool to tackle low assessed levels of technical performance in the OR. Gas, et al. reported that when performance is assessed carefully and remedial simulation is applied systematically with clearly-defined goals, performance shortfalls on skills station tasks can be corrected (25). The authors made use of the terms "poor performance" and "remediation" to describe trainee characteristics and actions taken, but these did not have a measured clinical context. In truth, the effectiveness of formal remediation of knowledge, behavior, or skills in surgical residency is not well studied. Similarly, the relationship of the need for remediation to attrition is also not well established, although we maintain that some performance characteristics may not be remediable and should appropriately result in residency program attrition. In a survey-based study of categorical residents in 21 American surgery residencies, Schwed, et al. reported that use of effective remediation correlated with lower attrition rates (26). Speculating on the reasons for this observation, the authors suggested that programs using remediation may take greater ownership of performance deficits and take greater pains to help residents correct performance deficits.

The belief that at least some low technical performance characteristics in trainees can be effectively addressed with education tools including lab-based simulation practice was one of the benefits we had hoped to achieve by building our Firefly-based assessment system. The current results show that with the use of a dynamic and widely-implemented framework of operative skills assessment and active modeling of lab-based training experiences, operative skill and autonomy can be improved after having been defined as insufficient. In this case, programmatic recognition of the need for focused development did not necessarily require defining a need for "remediation." There are expected variations in observed skills during the course of residency training (12). Without clear evidence of how these variations impact clinical outcomes, professional standing, or other career difficulties, assigning these descriptors implies a level of significance that might not have a consistent basis. That is not to say that the terms are not applicable or that targeted skills development is not of critical importance. There is, however, a need to frame the goals of such skills development around the evidence that it is of value, and that they contribute to clinical performance improvement. In our own program we have, somewhat arbitrarily, defined the need of "remediation" in a very formal sense to describe a state of escalation of concern about failing performance. By consensus, our institution's residency programs have further reserved the term for situations where success of corrective measures is truly in question and non-promotion or employment action may be justified. Labels or measures that stigmatize can negatively affect responsiveness to efforts to achieve improvement (27). In some settings, such labels have implications such as reportability to regulatory bodies, and can have further implications to future licensure or credentialing. None of the residents for whom data are reported here were identified as "failing" and the subjective observations made about the observed skills were generally in the context of expected level-appropriate skills. None of the learning plans were presented to participating residents as "remediation." The learning plans were formalized, however, with specific requirements, the most important of which was the message that supplemental training was mandatory and compliance would be monitored. In all instances, supplemental training occurred over a period of months and, in some situations, residents had to be reminded to resume sessions after missed sessions were reported by the Simulation Center staff.

Although the retrospectively aggregated data we report showed a temporary, correctable performance lag for selected residents, there are important limitations that must be noted that make it difficult to make detailed characterizations of performance changes or to comment on causation in regard to the educational interventions. Sweeping statements based on performance patterns for only four trainees are clearly unwarranted. The amount, frequency, and precise makeup of the supplemental training were not consistently recorded. The actual number of sessions, hours in training, and specific lab goals achieved for each resident were only known in general terms and there was no systematic accounting of self-directed practice sessions. There is also no information available on other opportunities for learning or other educational actions taken either in or out of the operating room that may have affected the longitudinal results of individual O-SCORE data. Although operative autonomy and operative skill are not synonymous, a recent collaborative examination of attending decision-making on awarding resident autonomy in the OR suggested that the most important determinant is residents' perceived performance (28). The scaled items used in the O-SCORE instrument infer level of competency based on the perceived need of the evaluator to do portions (or all) of the case. For results to be consistent between evaluators, a resident's opportunity to exercise autonomy would have to be granted on a fairly uniform basis. Despite sophisticated embedded mathematical tools in the Firefly platform to discern whether this occurs, varying thresholds for intervention between evaluators who, as surgeons of record, are in the position to skew O-SCORE results by their own biases, were difficult to control for in an analysis of this limited size. This can be studied further, however, by looking for patterns of "hawk" and "dove" grading behaviors that might be evident in larger data sets.

Our study strengths included wide use of a fairly well-studied assessment instrument, albeit in somewhat modified form. The O-SCORE tool has been shown to produce accurate and reproducible results in the evaluation of surgical competence in trainees, both in the operating room and in simulation (4,5). Our recent experience with use of Firefly-facilitated modified O-SCORE assessments showed that evaluations were completed and pushed electronically to the assessed residents rapidly, the process completed in the majority of cases within a few hours (6). However, even when available for use for the totality of resident cases performed, only 11% of the resident-performed laparoscopic cases received O-SCORE assessments during the 2016-19 review period. These were completed by a core group of trained evaluators all of whom were highly experienced full-time faculty minimally invasive surgeons. In the course of the program's formative education efforts, our hope was that these assessments contributed in a meaningful way to residents' performance feedback and provided a basis for performance improvement, in addition to keeping residency program leadership informed of performance issues. However, the success of lab-based interventions to help trainees add skills defined as lagging but necessary to clinical development is not a given. We would like to gain a greater degree of confidence that close tracking of resident assessment results provides a meaningful basis to model training and intervene early to ensure success in training efforts.

Until the current report, we had not used assessment data as a means of tracking the effectiveness of specific educational measures employed by the residency program. The use of the Firefly platform to comprehensively manage evaluative information enabled us to query and analyze grouped and individual data in order to address an educational quality question that would have been more cumbersome to answer without the availability of the platform. Other web-based systems for delivery of assessments and compilation of assessment data have been used successfully (29-31). All are examples of the application of technology to the problem of ensuring high quality evaluations and to the logistical problem of facilitating timely and frequent completion. However, the analysis of compiled performance data to ensure that larger program actions are helping to maintain the quality of education has not been a major focus of these efforts. We found that the integration of analytic tools into the same platform used for evaluation management is critical to monitoring the overall quality of educational processes. It is now standard practice for our team to not only examine individual resident progress with increasingly frequent use of these tools, but to also examine grouped data with the Firefly platform's analytic tools in order to determine if additions and changes in our educational program impact residents' clinical abilities.

TABLE 3

| Metric | Pre-Int. | Post-Int. | Non-Int. | Pre- vs Post-Int p-value | Pre- vs Non-Int p-value | Post- vs Non-Int p-value |
|---|---|---|---|---|---|---|
| Overall | 2.25 ± 0.43 | 3.40 ± 0.61 | 3.57 ± 1.02 | 0.000037 | 0.000089 | 0.35 |
| Tissue Handling | 2.12 ± 0.60 | 3.53 ± 0.72 | 3.56 ± 1.09 | 0.00028 | 0.00021 | 0.91 |
| Instrument Handling | 2.12 ± 0.78 | 3.40 ± 0.61 | 3.59 ± 1.1 | 0.0015 | 0.0029 | 0.30 |
| Bimanual Dexterity | 2.0 ± 0.71 | 3.33 ± 0.70 | 3.4 ± 1.32 | 0.00097 | 0.0011 | 0.76 |
| Visuospatial | 1.88 ± 0.6 | 3.47 ± 0.72 | 3.7 ± 1.13 | 0.000048 | 0.000058 | 0.26 |
| Efficiency/Flow | 2.0 ± 0.50 | 3.27 ± 0.57 | 3.38 ± 1.11 | 0.000085 | 0.000090 | 0.51 |

Table 3 Abbreviations: Pre-Int. = pre-intervention; Post-Int. = post-intervention; Non-Int = non-intervention

REFERENCES FOR EXAMPLE 5 ABOVE

1. Birkmeyer J D, Finks J F, O'Reilly A, Oerline M, Carlin A M, Nunn A R, Dimick J, Banerjee M, Birkmeyer N J; Michigan Bariatric Surgery Collaborative. Surgical skill and complication rates after bariatric surgery. N Engl J Med. 2013; 369(15):1434-42. https//doi: 10.1056/NEJMsa1300625.
2. Abid M A, Li Y W, Cummings C W, Bhatti N I. Patient outcomes as a measure of surgical technical skills: Does surgical competency matter? A systematic review. Otorinolaringologia. 2016; 66(4):99-106.
3. ACGME Program Requirements for Graduate Medical Education in General Surgery. https://www.acgme.org/Portals/0/PFAssets/Program Requirements/440_General-Surgery_2019. pdf?ver=2019-06-19-092818-273
4. Thanawala R, Jesneck J, Seymour N. Novel Educational Information Management Platform Improves the Surgical Skill Evaluation Process of Surgical Residents. J Surg Education. 2018; 75(6):e204-e211. https//doi: 10.1016/j.jsurg.2018.06.004.
5. MacEwan M J, Dudek N L, Wood T J, Gofton W T. Continued validation of the O-SCORE (Ottawa Surgical Competency Operating Room Evaluation): use in the simulated environment. Teach Learn Med. 2016; 28(1): 72-9. https//doi: 10.1080/10401334.2015.1107483.
6. Gofton W T, Dudek, N L, Wood T J, Balaa F, Hamstra S J. The Ottawa Surgical Competency Operating Room Evaluation (O-SCORE): a tool to assess clinical competence. Acad Med. 2012; 87(10): 1401-7. https//doi: 10.5555/2627435.2638586.
7. Berg B A. Markov Chain Monte Carlo Simulations and Their Statistical Analysis. Singapore. World Scientific Publishing Co. Pte. Ltd., 2004.
8. Hoffman M D, Gelman A. The No-U-Turn sampler: adaptively setting path lengths in Hamiltonian Monte Carlo. J Mach Learn Res. 2014; 15(1): 1593-1623.
9. McManus I C, Thompson M, Mollon J. Assessment of examiner leniency and stringency ('hawk-dove effect') in the MRCP (U K) clinical examination (PACES) using multi-facet Rasch modelling. BMC Med Educ. 2006 Aug. 18; 6:42. https//doi.org/10.1186/1472-6920-6-42.
10. Ahmed N, Devitt K S, Keshet I, Spicer J, Imrie K, Feldman L, Cools-Lartigue J, Kayssi A, Lipsman N, Elmi M, Kulkarni A V, Parshuram C, Mainprize T, Warren R J, Fata P, Gorman M S, Feinberg S, Rutka J. A systematic review of the effects of resident duty hour restrictions in surgery: impact on resident wellness, training, and patient outcomes. Ann Surg. 2014; 259(6): 1041-53. https//doi: 10.1097/SLA.0000000000000595.
11. Drake F T, Horvath K D, Goldin A B, Gow K W. The general surgery chief resident operative experience: 23 years of national ACGME case logs. JAMA Surg. 2013; 148(9):841-7. https//doi: 10.1001/jamasurg.2013.2919.
12. Quillin R C 3rd, Cortez A R, Pritts T A, Hanseman D J, Edwards M J, Davis B R. Operative variability among residents has increased since implementation of the 80-hour workweek. J Am Coll Surg. 2016; 222(6):1201-10. doi: 10.1016/j.jamcollsurg.2016.03.004. Epub 2016 Mar. 18.
13. Bell R H Jr. Why Johnny cannot operate. Surgery. 2009; 146(4):533-42. https//doi: 10.1016/j.surg.2009.06.044.
14. Hashimoto D A, Bynum W E 4th, Lillemoe K D, Sachdeva A K. See More, Do More, Teach More: Surgical Resident Autonomy and the Transition to Independent Practice. Acad Med. 2016; 91(6):757-60. https//doi: 10.1097/ACM.0000000000001142.
15. Bucholz E M, Sue G R, Yeo H, Roman S A, Bell R H Jr, Sosa J A. Our trainees' confidence results from a national survey of 4136 U S general surgery residents. Arch Surg. 2011; 146(8):907-914. https//doi:10.1001/archsurg.2011.178
16. Mattar S G, Alseidi A A, Jones D B, Jeyarajah D R, Swanstrom L L, Aye R W, Wexner S D, Martinez J M, Ross S B, Awad M M, Franklin M E, Arregui M E, Schirmer B D, Minter R M. General surgery residency inadequately prepares trainees for fellowship: results of a survey of fellowship program directors. Ann Surg. 2013; 258(3):440-9. https//doi: 10.1097/SLA.0b013e3182a191ca.

17. Jarman B T, O'Heron C T, Kallies K J, Cogbill T H. Enhancing Confidence in Graduating General Surgery Residents: Establishing a Chief Surgery Resident Service at an Independent Academic Medical Center. J Surg Educ. 2018; 75(4):888-894. https//doi: 10.1016/j.jsurg.2017.12.012. Epub 2018 Feb. 3.
18. Luc J G Y, Antonoff M B. Active Learning in Medical Education: Application to the Training of Surgeons. J Med Educ Curric Dev. 2016 May 4; 3. pii: JMECD.S18929. doi: 10.4137/JMECD.S18929. eCollection 2016 January-December
19. Nagendran M, Gurusamy K S, Aggarwal R, Loizidou M, Davidson B R. Virtual reality training for surgical trainees in laparoscopic surgery. Cochrane Database Syst Rev. 2013; (8): CD006575. https//doi: 10.1002/14651858.CD006575.pub3.
20. Papanikolaou I G, Haidopoulos D, Paschopoulos M, Chatzipapas I, Loutradis D, Vlahos N F. Changing the way we train surgeons in the 21th century: A narrative comparative review focused on box trainers and virtual reality simulators. Eur J Obstet Gynecol Reprod Biol. 2019; 235:13-18. https//doi: 10.1016/j.ejogrb.2019.01.016.
21. Hanks J B. Simulation in Surgical Education: Influences of and Opportunities for the Southern Surgical Association. J Am Coll Surg. 2019; 228(4):317-328. https//doi: 10.1016/j.jamcollsurg.2018.12.029. Epub 2019 Jan. 17.
22. Cox T, Seymour N, Stefanidis D. Moving the Needle: Simulation's Impact on Patient Outcomes. Surg Clin North Am. 2015; 95(4):827-38. https//doi: 10.1016/j.suc.2015.03.005.
23. Kim S C, Fisher J G, Delman K A, Hinman J M, Srinivasan J K. Cadaver-Based Simulation Increases Resident Confidence, Initial Exposure to Fundamental Techniques, and May Augment Operative Autonomy. J Surg Educ. 2016; 73(6):e33-e41. https//doi: 10.1016/j.jsurg.2016.06.014.
24. Lesch H, Johnson E, Peters J, Cendan J C. V R simulation leads to enhanced procedural confidence in surgical trainees. J Surg Educ. 2020; 77(1):213-218. https//doi: 10.1016/j.jsurg.2019.08.008.
25. Gas B L, Buckarma E H, Mohan M, Pandian T K, Farley D R. Objective Assessment of General Surgery Residents Followed by Remediation. J Surg Educ. 2016; 73(6):e71-e76. https//doi: 10.1016/j.jsurg.2016.07.002.
26. Schwed A C, Lee S L, Salcedo E S, et al. Association of General Surgery Resident Remediation and Program Director Attitudes With Resident Attrition. JAMA Surg. 2017; 152(12):1134-1140. https//doi:10.1001/jamasurg.2017.2656
27. Kalet A, Chou C L, Ellaway R H. To fail is human: remediating remediation in medical education. Perspect Med Educ. 2017; 6(6):418-424. https//doi: 10.1007/s40037-017-0385-6.
28. Williams R G, George B C, Meyerson S L, Bohnen J D, Dunnington G L, Schuller M C, Torbeck L, Mullen J T, Auyang E, Chipman J G, Choi J, Choti M, Endean E, Foley E F, Mandell S, Meier A, Smink D S, Terhune K P, Wise P, DaRosa D, Soper N, Zwischenberger J B, Lillemoe K D, Fryer J P; Procedural Learning and Safety Collaborative. What factors influence attending surgeon decisions about resident autonomy in the operating room? Surgery. 2017; 162(6):1314-1319. https//doi: 10.1016/j.surg.2017.07.028.
29. Wohaibi E M, Earle D B, Ansanitis F E, Wait R B, Fernandez G, Seymour N E. A new web-based operative skills assessment tool effectively tracks progression in surgical resident performance. J Surg Educ. 2007; 64(6): 333-41.
30. Wagner J P, Chen D C2, Donahue T R, Quach C, Hines O J, Hiatt J R, Tillou A. Assessment of resident operative performance using a real-time mobile Web system: preparing for the milestone age. J Surg Educ. 2014; 71(6): e41-6. https//doi: 10.1016/j.jsurg.2014.06.008.
31. Bohnen J D, George B C, Williams R G, Schuller M C, DaRosa D A, Torbeck L, Mullen J T, Meyerson S L, Auyang E D, Chipman J G, Choi J N, Choti M A, Endean E D, Foley E F, Mandell S P, Meier A H, Smink D S, Terhune K P, Wise P E, Soper N J, Zwischenberger J B, Lillemoe K D, Dunnington G L, Fryer J P; Procedural Learning and Safety Collaborative (PLSC). The Feasibility of Real-Time Intraoperative Performance Assessment With SIMPL (System for Improving and Measuring Procedural Learning): Early Experience From a Multi-institutional Trial. J Surg Educ. 2016; 73(6):e118-e130. https//doi: 10.1016/j.jsurg.2016.08.010.
32. Gundle K R, Mickelson D T, Cherones A, Black J, Hanel D P. Rapid Web-Based Platform for Assessment of Orthopedic Surgery Patient Care Milestones: A 2-Year Validation. J Surg Educ. 2017; 74(6):1116-1123. https//doi: 10.1016/j.jsurg.2017.05.001.
33. Van Heest A E, Agel J, Ames S E, Asghar F A, Harrast J J, Marsh J L, Patt J C, Sterling R S, Peabody T D. Resident Surgical Skills Web-Based Evaluation: A Comparison of 2 Assessment Tools. J Bone Joint Surg Am. 2019 Mar. 6; 101(5):e18. https//doi: 10.2106/JBJS.17.01512.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

At certain points throughout some of the Examples of the specification, some references are referred to using a number in parentheses. Those numbers correspond to the references listed at the end of that particular example. Other references are cited within other parts of the specification and other references are cited separately.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps of the methods or components of the compositions, it is also contemplated that the methods and compositions consist essentially of, or consist of, the recited steps or components. Furthermore, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

What is claimed is:

1. A web-based data management platform for accelerating the acquisition of a requisite skill level for a healthcare professional and providing users of the platform with real-time skill acquisition ranking information of each healthcare professional, the platform comprising:
  a computer, a server or data storage system, a user interface, a non-transitory computer readable medium storing computer program instructions, software for analyzing the input data and providing an output, and a data array, wherein the platform is configured to perform acts comprising:
  a) acquiring updated data from disparate systems of a preselected set of tasks, a list of completed tasks for a healthcare professional, evaluations of task performance for the healthcare professional, and a clinical schedule that defines the tasks available to be performed by the healthcare professional, wherein the updated data acquired is in a non-standardized format;
  b) converting the acquired data into a standardized data format;
  c) statistically modeling the professional's progress in acquiring the requisite skill level based on the standardized acquired data, the method of statistical modeling comprising the steps of:
    performing a Markov Chain Monte Carlo (MCMC) statistical sampling method calculation from distributions of relevant parameters for each of a peer group of subordinate healthcare professionals and associated supervisory healthcare professionals for each task in step a), and based thereupon
    estimating a posterior distribution of learning curve parameters of each subordinate healthcare professional for each step of each task in step a),
  d) comparing the statistical model of the professional's progress to a preselected set of standards to rank the healthcare professional versus the standards and providing that rank to users via the user interface so that each user has real-time access to up-to-date ranking information;
  e) integrating the standardized acquired data into a workflow that efficiently allocates the tasks available and simultaneously facilitates the acquisition of the requisite skill level by the healthcare professional; and
  f) prescribing a next task to be performed to by the healthcare professional according to the workflow and the statistically modeled progress of the professional.

2. A web-based data management platform according to claim 1; the platform further configured to perform acts comprising: for accelerating the acquisition of a requisite skill level for a healthcare professional, comprising:
  a computer, a server or data storage system, a user interface, a non-transitory computer readable medium storing computer program instructions, software for analyzing the input data and providing an output, and a data array, wherein the platform is configured to perform acts comprising:
    a) acquiring updated data from disparate systems of a preselected set of tasks, a list of completed tasks for a healthcare professional, evaluations of task performance for the healthcare professional, and a clinical schedule that defines the tasks available to be performed by the healthcare professional, wherein the updated data acquired is in a non-standardized format;
    b) converting the acquired data into a standardized data format;
    c) statistically modeling the professional's progress in acquiring the requisite skill level based on the standardized acquired data, the method of statistical modeling comprising the steps of:
      i) collecting performance evaluations from a group of supervisory healthcare professionals for the performance of one or more selected tasks for a peer group of subordinate healthcare professionals;
      ii) assessing the clinical complexity of each task from step i);
      iii) compiling and standardizing the evaluations collected from step i) versus predetermined standards for the successful completion of the one or more tasks;
      iv) determining the prior distributions for relevant parameters for each supervisory healthcare professional and for each subordinate healthcare professional for each task based on steps ii) and iii);
      v) performing a Markov Chain Monte Carlo (MCMC) statistical sampling method calculation from the output of step iv) to determine posterior distributions of the resultant learning curves for the subordinate healthcare professionals;
      vi) from the posterior distributions from step v), determining learning curves for each subordinate healthcare professional for each step of the one or more tasks; and
      vii) comparing the output learning curve for each subordinate healthcare professional from step vi) to that of the peer group to determine the performance and/or proficiency of each subordinate health care professional,
    d) comparing the statistical model of the professional's progress to a preselected set of standards to rank the healthcare professional versus the standards and providing that rank to users via the user interface so that each user has real-time access to up-to-date ranking information;
    e) integrating the standardized acquired data into a workflow that efficiently allocates the tasks available and simultaneously facilitates the acquisition of the requisite skill level by the healthcare professional; and
    f) prescribing a next task to be performed to by the healthcare professional according to the workflow and the statistically modeled progress of the professional.

3. The web-based data management platform according to claim 1 wherein the healthcare professional is selected from the group consisting of medical students, interns, residents, fellows, doctors, physician assistants, nurses, nurses' aides, and medical technicians.

4. The web-based data management platform according to claim 2 involving a teaching situation, including a supervisory healthcare professional and a subordinate healthcare professional.

5. The web-based data management platform according to claim 1 wherein the user interface is selected from the group consisting of a graphical user interface, a command-line interface, or a menu driven interface.

6. The web-based data management platform according to claim 5 wherein the user interface is a graphical user interface.

7. The web-based data management platform according to claim 6, wherein the graphical user interface is configured to augment a clinical schedule with case-based actions; the graphical user interface comprising:
- a first element showing a staff assignment for a clinical encounter; and
- a second element juxtaposed to the first element and showing a button, a tag, a status label, or an actionable link for an encounter-related activity, such as case logging, performance evaluation, data quality control, and accessing medical educational content.

8. The web-based data management platform according to claim 1 that is Health Insurance Portability and Accountability Act compliant.

\* \* \* \* \*

UNITED STATES PATENT AND TRADEMARK OFFICE
CERTIFICATE OF CORRECTION

PATENT NO.         : 11,145,407 B1
APPLICATION NO.    : 16/853160
DATED              : October 12, 2021
INVENTOR(S)        : Jonathan Lee Jesneck and Ruchi Mrugesh Thanawala Page 1 of 1

It is certified that error appears in the above-identified patent and that said Letters Patent is hereby corrected as shown below:

In the Claims

In Claim 2, replace Column 41, Line 55 with the following:
--for accelerating the acquisition of a requisite--

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*